(12) United States Patent
Adourian et al.

(10) Patent No.: US 8,321,154 B2
(45) Date of Patent: Nov. 27, 2012

(54) METHODS FOR DETECTING CORONARY ARTERY DISEASE

(75) Inventors: Aram S. Adourian, Woburn, MA (US); Doris Damian, West Newton, MA (US); Amir Handzel, Watertown, MA (US)

(73) Assignee: BG Medicine, Inc., Waltham, MA (US)

( * ) Notice: Subject to any disclaimer, the term of this patent is extended or adjusted under 35 U.S.C. 154(b) by 252 days.

(21) Appl. No.: 12/593,149

(22) PCT Filed: Mar. 24, 2008

(86) PCT No.: PCT/US2008/003846
§ 371 (c)(1),
(2), (4) Date: Mar. 16, 2010

(87) PCT Pub. No.: WO2008/118413
PCT Pub. Date: Oct. 2, 2008

(65) Prior Publication Data
US 2010/0173346 A1    Jul. 8, 2010

Related U.S. Application Data

(60) Provisional application No. 60/920,333, filed on Mar. 26, 2007.

(51) Int. Cl.
*G01N 33/53* (2006.01)
*G01N 33/48* (2006.01)
(52) U.S. Cl. .............. 702/23; 702/19; 435/7.1
(58) Field of Classification Search .......... None
See application file for complete search history.

(56) References Cited

U.S. PATENT DOCUMENTS 4,775,483 A    10/1988    Mookerjea et al.

OTHER PUBLICATIONS

Kannel, "Range of Serum Cholesterol Values in the Population Developing Coronary Artery Disease," The American Journal of Cardiology, 76(9):69C-77C, Sep. 28, 1995.
Nikkari, "Serum Fatty Acids and Coronary Heart Disease in Finnish Populations," Progress in Lipid Research, 25:437-450, 1986.
Simon et al., "Serum Fatty Acids and the Risk of Coronary Heart Disease," American Journal of Epidemiology, 142 (5):469-476, 1995.
Wilson et al., "Prediction of Coronary Heart Disease Using Risk Factor Categories," Circulation, 97(18):1837-1847, 1998.
Supplementary European Search Report for EP Application No. 10191937, mailed Sep. 22, 2011, 10 pgs.
Kannel, "Range of Serum Cholesterol Values in the Population Developing Coronary Artery Disease," Am J Cardiol, 1995; 76:69C-77C.
Maree, "Aspirin and coronary artery disease," Thromb Haemost, 2004; 92:1175-81.
Wilson, et al., "Prediction of Coronary Heart Disease Using Risk Factor Categories," Circulation, 1998; vol. 97, No. 18, pp. 1837-1847.
PCT International Search Report for PCT/US2008/003846, mailed Sep. 24, 2008, 16 pgs.
PCT Written Opinion of the International Searching Authority for PCT/US2008/003846, 12 pgs.

*Primary Examiner* — Michael Borin
(74) *Attorney, Agent, or Firm* — Burns & Levinson LLP

(57) ABSTRACT

Markers are provided for detecting coronary artery disease. Levels of these markers are indicative of a patient being at risk of having or developing coronary artery disease.

4 Claims, 12 Drawing Sheets

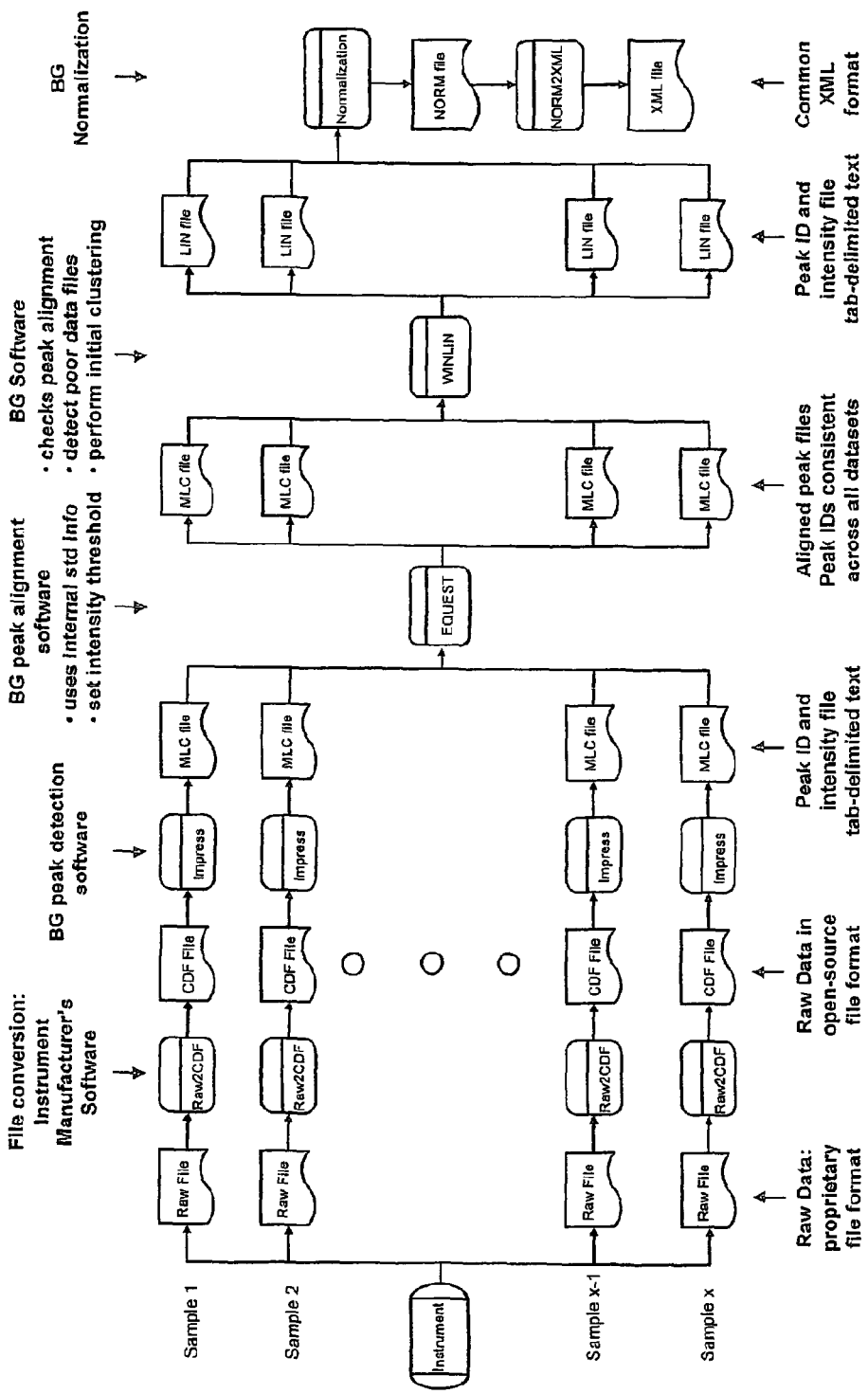
Figure 2a  LC/MS and GC/MS data pre-processing work flow diagram.

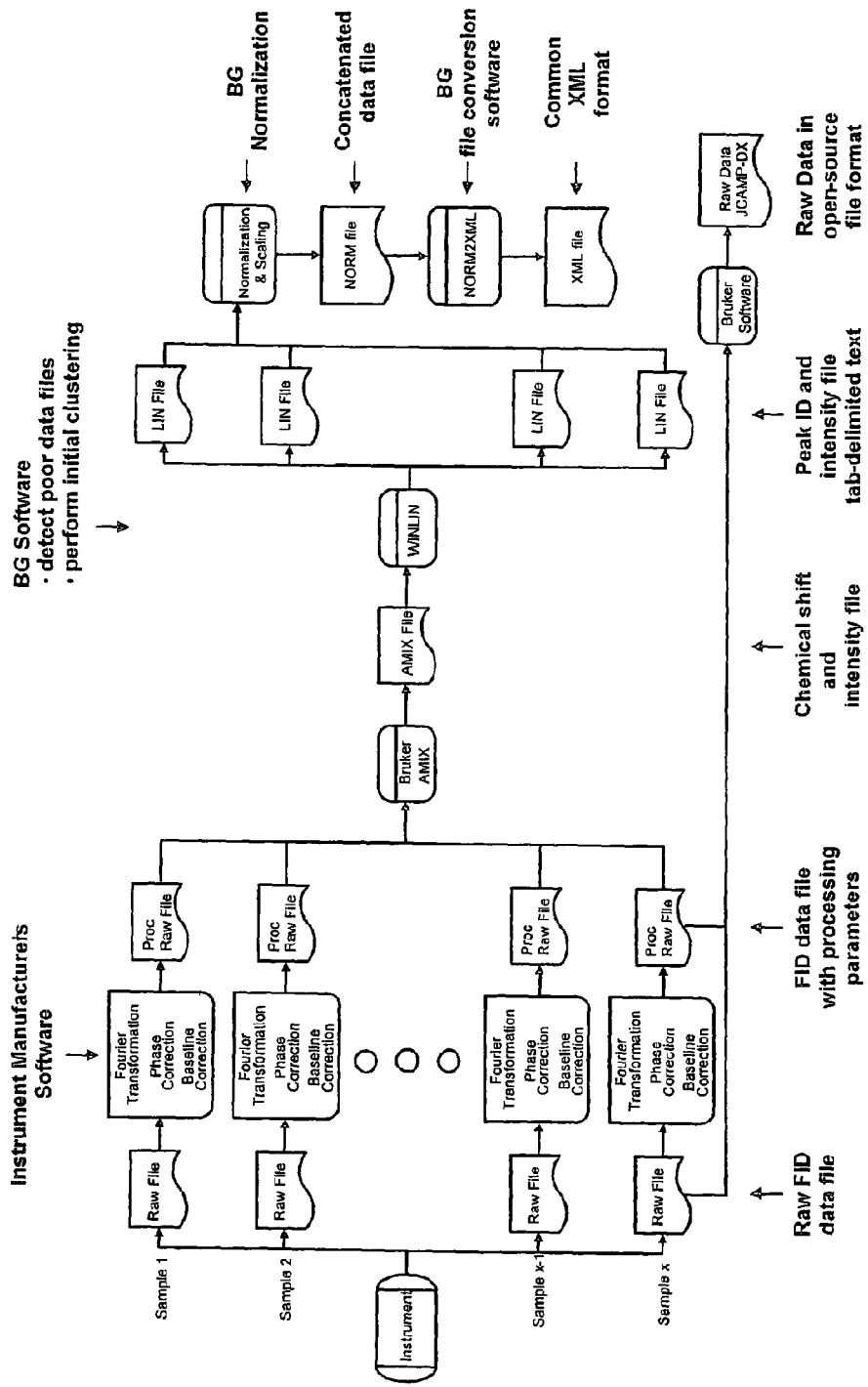
Figure 2b  NMR data pre-processing work flow diagram.

Figure 4

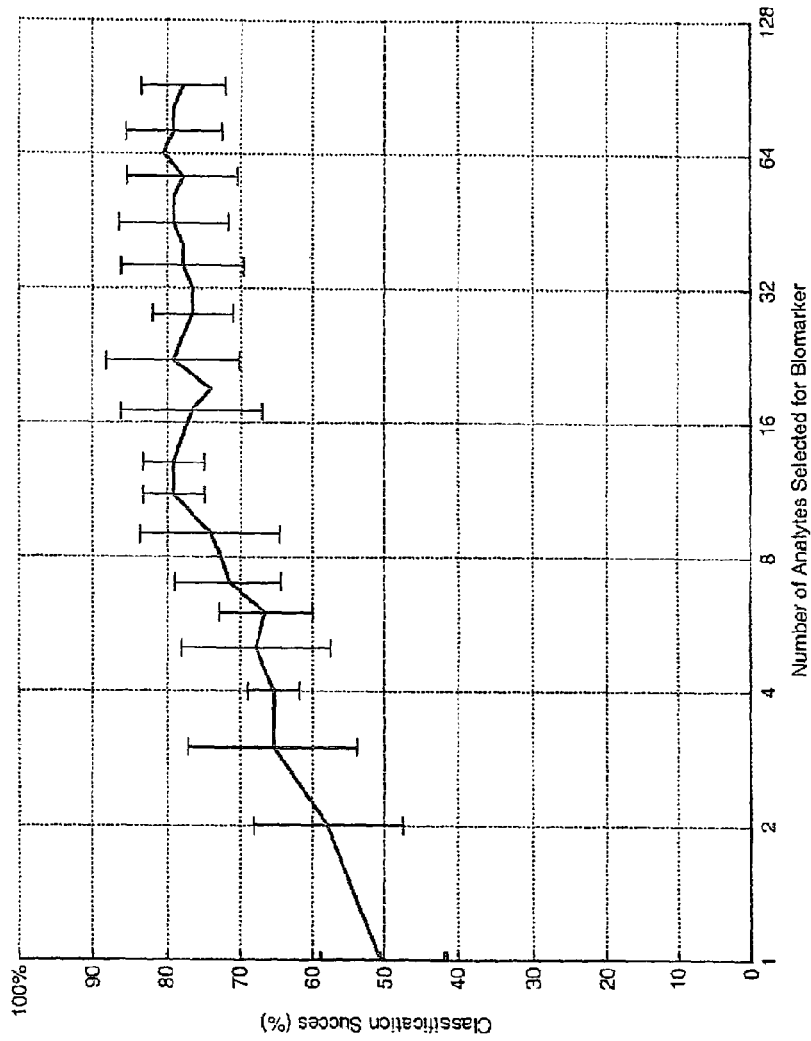

Cross-validation performance as a function of number of analytes in classifier for the data set comprising 40 CAD>0 and 40 CAD=0 samples. The algorithm described works from right to left—i.e. starting with 94 analytes and reducing by Recursive Feature Elimination until only one analyte remains. The bars represent the standard errors of the multiple cross-validation rounds.

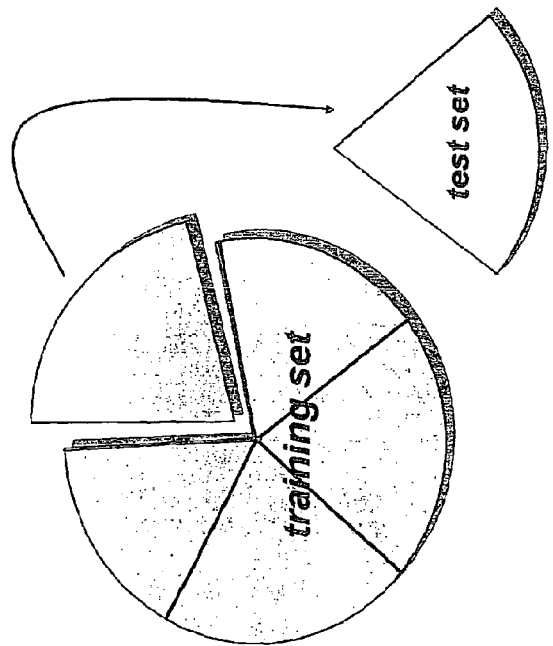

Figure 5

The principle of 'Cross-Validation'. From a complete set of samples, a 'test set' is extracted and temporarily left out of the analysis. The re-introduction of the test set allows for the calculation of sensitivity and specificity for the samples in the test set. This process is repeated many times, and each time a different, randomly chosen test is left out. In the present study, typically six CAD>0 and six CAD=0 samples, chosen randomly, were left out for each iteration. The number of such iterations tested is of the order 10, and at the end of the exercise a mean and standard error is calculated and reported.

METHODS FOR DETECTING CORONARY ARTERY DISEASE

CROSS REFERENCE TO RELATED APPLICATIONS

This application is a national phase application under 35 U.S.C. §371 of International Patent Application No. PCT/US2008/003846, filed Mar. 24, 2008, which claims priority to and the benefit of U.S. Provisional Patent Application No. 60/920,333, filed Mar. 26, 2007, the entire disclosures of each of which are incorporated by reference herein.

FIELD OF THE INVENTION

The invention relates to methods for detecting coronary artery disease. More specifically, the invention relates to methods for screening an individual for being at risk of having or developing coronary artery disease by using one or more markers.

BACKGROUND

Coronary artery disease, also referred to as coronary heart disease or heart disease, is the leading cause of death for both men and women in the United States. Coronary artery disease afflicts more than fourteen million people in the United States. Many people are afflicted with the disease without suffering symptoms or undergoing treatment.

Coronary artery disease involves the coronary arteries becoming partially clogged, leading to a narrowing known as stenosis. This blockage limits the flow of blood from the coronary arteries, which are the major arteries supplying oxygen to the heart. If coronary arteries are clogged and unable to expand, the heart is deprived of oxygen, a condition known as myocardial ischemia. With a coronary arterial stenosis, chest pain or pressure, called angina, may occur. When the blockage is sufficient to prevent the flow of blood to the heart, the result is heart attack, also known as myocardial infarction or heart muscle death.

Over one hundred billion dollars are spent annually on coronary artery disease. Much of this cost is related to medication, hospitalization, caregiving, such as nursing home care and in-home day care. Accordingly, to the extent that coronary artery disease could be affirmatively diagnosed during an individual's lifetime, medical treatment might be provided that might provide benefits by slowing or reversing the progression of the disease, reducing morbidity and mortality rates and improving, and improving quality of life.

Thus, there remains a need for diagnostic methods for coronary artery disease. In particular, reliable and cost-effective methods and compositions are needed to allow for diagnosis of coronary artery disease.

SUMMARY OF THE INVENTION

Markers have been identified in blood that are useful in assessing coronary artery disease status in a patient. The levels of these markers, when different from a standard, are indicative of coronary artery disease. Methods according to the invention utilize some or all of the markers to detect coronary artery disease. Specifically, an individual can be screened for being at risk of having or developing coronary artery disease by using one or more of these markers and determining if the levels of these markers are different from a standard.

Markers have been identified that can be chosen to create assays of varying specificity and sensitivity for detecting coronary artery disease. Specificity is the true negative rate, or the screening test's ability to correctly identify the absence of disease. In other words, it is the percentage of people in a group who truly do not have the disease. A test with high specificity has few false positives. Sensitivity is the true positive rate, or the screening test's ability to identify true disease. In other words, it is the percentage of people in a group who are detected as positives who truly are positive for the disease. A test with high sensitivity has few false negatives. Typically, the more markers that are used in the assay, the better the sensitivity and the specificity of the assay. Specifically, when fifteen (first-choice) markers are used, a sensitivity of about 87% and a specificity of about 89% can be obtained.

The markers of the present invention can be useful for more than just diagnosing coronary artery disease. The markers can be used to screen candidate drugs for treating coronary artery disease or to determine the efficacy of a drug treatment on an individual with coronary artery disease. The markers also can be used to identify individuals whose health needs to be monitored. Also, the markers can be used to validate an animal model for coronary artery disease.

In one aspect, the invention provides a method for screening an individual for being at risk of having or developing coronary artery disease. An amount of each at least one marker in a sample from a patient are compared with each of the at least one marker from a standard. A difference in the amount of each of the at least one marker between the sample and the standard indicates a positive screen. The markers are selected from 2-hydroxy-benzoic acid, alanine, C14:0 SPM, C16:0 SPM, C18:0 LPC, C18:2, C18:2 CE, C18:2 LPC, C20:4 CE, C20:4 LPC, C21:0 SPM, C22:0 SPM, C22:6 CE, C23:0 SPM, C24:0 SPM, C26:0 PC, C32:1 PC, C32:2 PC, C34:2 PC, C34:3 PC, C34:4 PC, C36:2 PC, C36:3 PC, C40:6 PC, C46:0 TG, C54:5 TG, C56:7 TG, cholesterol, creatinine, creatine, formate, glutamic acid, glycerol, hexadecanoic acid, histidine, isoleucine, lipid (mainly VLDL), lysine, methylphenol, phenylalanine, 5-oxo-L-proline, proline, and valine, where: "PC", phosphatidylcholine; "LPC", lysophosphatidylcholine; "TG", triglyceride; "SPM", sphingomyelin; "CE", cholesterol ester. Further, the nomenclature CX:Y indicates, for a molecule of SPM, TG, CE or LPC, X number of total carbon atoms in the fatty acid portion(s) of the molecule, and Y number of double-bonds in the fatty acid portion(s) of the molecule, and the analyte identified as "C18:2" is the fatty acid molecule with scientific name "9,12-octadecadienoic acid" and common name "linoleic acid."

In another aspect, the invention provides a method for screening an individual for being at risk of having or developing coronary artery disease. An amount of each at least two markers in a sample from a patient are compared with each of the at least two markers from a standard. The markers are selected from C18:3 cholesterol ester, C32:1 phosphatidylcholine, alanine, lipid (mainly VLDL), lysine, hexadecanoic acid, C36:2 phosphatidylcholine, formate, C32:2 phosphatidylcholine, C18:2 (linoleic acid), cholesterol, C18:2 lysophosphatidylcholine, C36:3 phosphatidylcholine, C34:4 phosphatidylcholine, C34:3 phosphatidylcholine.

In various embodiments of this aspect of the method, the amount of each of at least three markers can be compared, the amount of each of at least four markers can be compared, the amount of each of at least five markers can be compared, the amount of each of at least six markers can be compared, the amount of each of at least seven markers can be compared, the amount of each of at least eight markers can be compared, the amount of each of at least nine markers can be compared, the amount of each of at least ten markers can be compared, the amount of each of at least eleven markers can be compared, the amount of each of at least twelve markers can be compared, the amount of each of at least thirteen markers can be compared, the amount of each of at least fifteen markers can be compared, or the amount of each of at least fifteen markers can be compared.

Various methods can be used for detecting the amount of each of the at least one marker in any of the aspects as described above, including immunoassay, mass spectroscopy, chromatography, chemical analysis, a calorimetric assay, spectrophotometric analysis, electrochemical analysis, and nuclear magnetic resonance. It is contemplated, however, that other analytical methods may be useful in the detection of the markers as well. Additionally, the methods described above and throughout the specification, can be performed on samples including a body fluid sample. For example, the methods of the invention may be performed on whole blood, blood plasma, blood serum, cerebrospinal fluid, saliva, urine, seminal fluid, breast nipple aspirate, pancreatic fluid, and combinations thereof. It is contemplated, however, that the methods of the invention also may be useful in detecting the markers in other body fluid samples or tissue samples. Additionally, the standard can be obtained from at least one healthy person, the healthy person having a predetermined dietary intake for a predetermined time before sampling. Moreover, the sample can be obtained from a patient of the same sex as the at least one healthy person, the patient having the same predetermined dietary intake for the same predetermined time before sampling as the at least one healthy person.

BRIEF DESCRIPTION OF THE DRAWINGS

The foregoing and other objects, features, and advantages of the invention described above will be more fully understood from the following description of various illustrative embodiments, when read together with the accompanying drawings. In the drawings, like reference characters generally refer to the same parts throughout the different views. The drawings are not necessarily to scale, and emphasis instead is generally placed upon illustrating the principles of the invention.

FIG. 2a shows a data preprocessing workflow for data derived from liquid chromatography and mass spectrometry, and gas chromatography and mass spectrometry, bioanalytical sample analysis platfroms.

FIG. 2b shows a data preprocessing workflow for data derived from proton nuclear magnetic resonance bioanalytical sample analysis platfroms

FIG. 4 shows an exemplary plot of "Cross-Validation Performance" on data sets as a function of the number of markers.

FIG. 5 shows a shematic of the "Cross Validation" principle.

DETAILED DESCRIPTION

Figure 1:
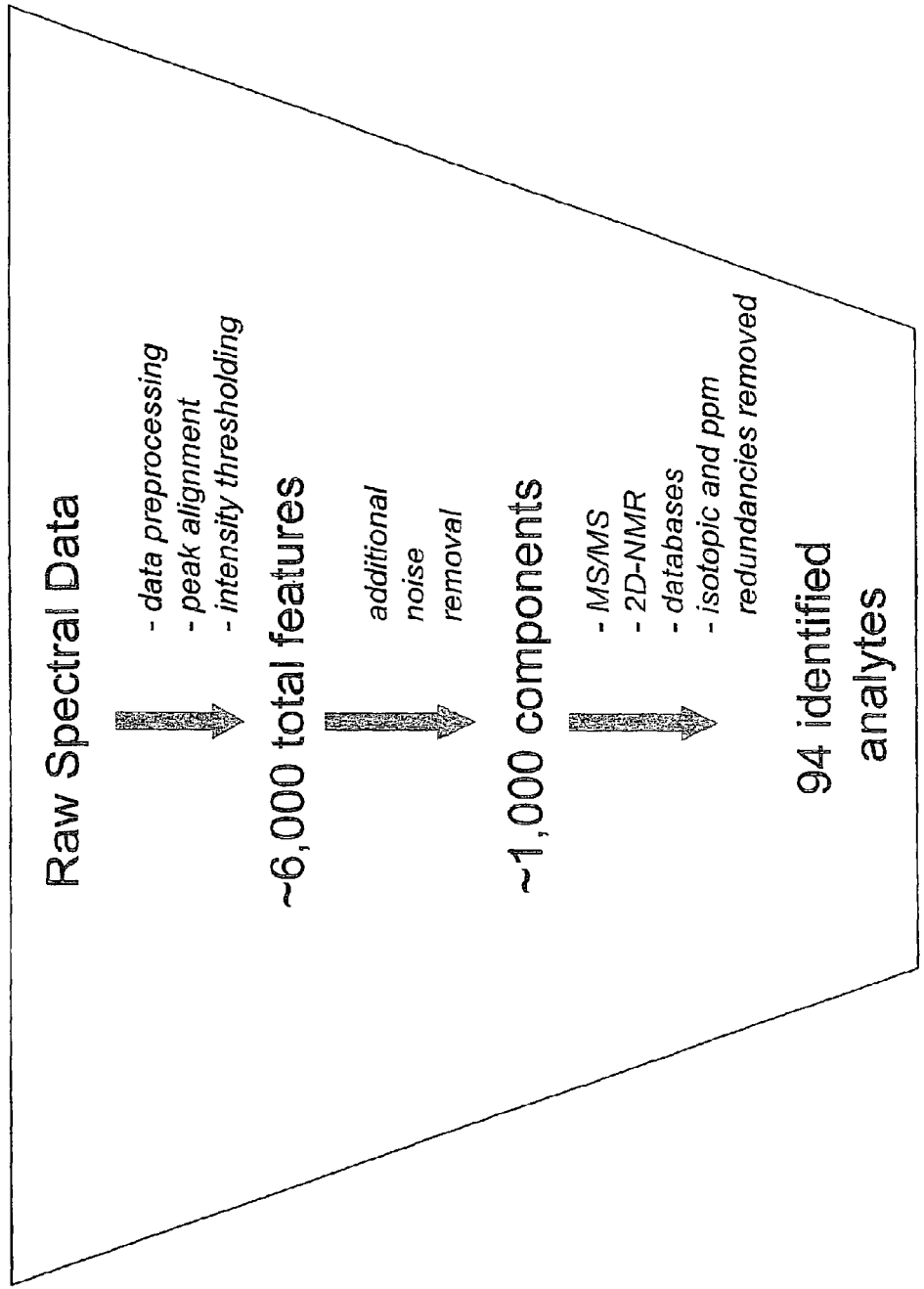
FIG. 1 shows a schematic of the progression from raw spectral data to identified analytes.

Markers have been identified that are predictive of coronary artery disease. When one or more of these markers are present in a body fluid sample from an individual in amounts different than those in a standard, they are indicative that the individual is at risk of having or developing coronary artery disease.

Fifteen (first-choice) markers have been identified. Certain methods according to the invention utilize two or more of these markers to detect coronary artery disease. Specifically, a sample from an individual can be screened to determine whether the sample contains levels of two or more of each of these markers that are different from a standard sample. If the sample contains an amount of each of two or more of these markers that is different from the amount of these markers in a standard, the screen is considered a "positive screen" (i.e., the individual is at risk of having or developing coronary artery disease). Greater sensitivity and specificity in classifying coronary artery disease samples can be obtained, typically, by using a greater number of the fifteen markers. The samples potentially containing these markers can be drawn from multiple biological sample types (e.g., body fluids, tissue, cells) obtained from multiple sources (e.g., whole blood, blood plasma, blood serum, urine, cerebrospinal fluid, epithelial cells, and endothelial cells). It should be understood that all possible combinations of the markers disclosed herein (and not just the fifteen (first-choice) markers) can be used in methods according to the invention.

Using the methodology described more fully in Example 1, the fifteen (first-choice) markers were identified. Briefly, through a specific analytical classification protocol, a set of spectral peaks were obtained. These peaks characterize specific molecules. Utilizing these peaks (which include many more peaks than just fifteen), fifteen (first-choice) peaks were identified (as well as other preferred peaks as described below). Insofar as peaks characterize molecules, identifying fifteen (first-choice) peaks from among a much larger number of peaks means that the markers are chosen from a group of molecules including more than the fifteen molecules corresponding to the fifteen (first-choice) markers. The markers (i.e., the molecules) may be any type of a molecule. The markers (molecules) include, but are not limited to, proteins, peptides, amino acids, lipids, steroids, nucleic acids, metabolites and elements. Table 0 provides specific molecules comprising the fifteen (first-choice) peaks (i.e., identifying the chosen markers). The final column of Table 2 rank-orders the peaks by weight. Accordingly, the highest weight peak is ranked number 1 and the lowest weight peak is ranked number 15.

TABLE 0

| Analyte | Coefficient (arb. units) |
| --- | --- |
| C18:3 Cholesterol ester | 0.42 |
| C32:1 Phosphatidylcholine | 0.33 |
| Alanine | 0.31 |
| Lipid (mainly VLDL) | 0.30 |

TABLE 0-continued

| Analyte | Coefficient (arb. units) |
| --- | --- |
| Lysine | 0.30 |
| Hexadecanoic acid | 0.25 |
| C36:2 Phosphatidylcholine | 0.24 |
| Formate | 0.23 |
| C32:2 Phosphatidylcholine | 0.21 |
| C18:2 (Linoleic Acid) | 0.20 |
| Cholesterol | 0.18 |
| C18:2 Lyso-phosphatidylcholine | 0.18 |
| C36:3 Phosphatidylcholine | 0.17 |
| C34:4 Phosphatidylcholine | 0.04 |
| C34:3 Phosphatidylcholine | 0.01 |

Now that the markers (i.e., any of the fifteen first-choice markers) are known, they can be used to screen an individual to determine whether the amount of each of two or more of these markers in a sample from the individual is different from the amount of each of the two or more markers from a standard, classifying the individual, to a certain specificity and sensitivity, as having or being at risk of developing coronary artery disease. Based on the number of markers examined, the desired sensitivity and specificity of the assay can be chosen (e.g., FIG. 4). The standard can be an actual sample or previously-generated empirical data. The standard can be obtained from a known normal person. The known normal person can be a healthy person and can have a predetermined dietary intake for a predetermined time before sampling. Moreover, the sample can be obtained from a known normal person of the same sex as the patient. Alternatively, the markers could be compared to those of a known coronary artery disease patient, in which case the similarity between the two samples would be examined. Various techniques and/or kits can be used by a medical professional for screening patient samples in order to determine the level and/or amount of a particular marker in a patient sample. Examples of such assays are described below and include, but are not limited to, an immunoassay, mass spectroscopy, chromatography, a chemical analysis, a colorimetric assay, a spectrophotometric analysis, an electrochemical analysis, and nuclear magnetic resonance. Additionally, such assays can be performed on any biological sample including whole blood, blood plasma, blood serum, cerebrospinal fluid, saliva, urine, seminal fluid, breast nipple aspirate, pancreatic fluid, and combinations thereof. These assays are chosen based on which are best suited to detect a particular marker as well as which are best suited for use with a particular biological sample. Accordingly, multiple assays may be used to detect the desired markers, and samples may be analyzed from one or more sources.

A marker can be detected and/or quantified by using one or more separation methods. For example, suitable separation methods may include a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, fourier transform mass spectrometry (FTMS) and ion trap. Spectrometric techniques that can also be used include resonance spectroscopy and optical spectroscopy.

Other suitable separation methods include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE), or other chromatographic techniques, such as thin-layer, gas or liquid chromatography, or any combination thereof. In one embodiment, the biological sample to be assayed may be fractionated prior to application of the separation method.

Tandem linking of chromatography (for example liquid chromatography ("LC") and mass spectrometry ("MS") is useful for detecting and quantifying one or more of the markers. LC is used to separate the molecules, which may include a marker, in a sample from an individual. A small amount of the sample, dissolved in a solvent, is injected into the injection port of the LC device, which is kept at a high temperature. The LC column of the device contains a solid substrate that can be either polar or non-polar. Because of differing polarities of the molecules in the sample, the molecules will have differing affinities for the solid substrate in the column and will elute at different times. The stronger the affinity of the molecule to the substrate, the longer the retention time of the molecule in the column. As the molecules exit the column, they enter the mass spectrometer. The mass spectrometer ionizes the molecules. In the tandem mass spectrometry mode, if the system is standardized properly, each compound sent into a mass spectrometer fragments into ions of various masses and abundances forming a signature pattern unique to that substance. By comparing the tandem mass spectrograph of each peak to a computerized database, the computer is usually able to identify the molecules with a high degree of certainty. Alternately, or additionally, this comparison may be carried out by human inspection. Once an identity is established, the computer integrates the area under each peak and thereby determines the relative quantity of each molecule in the mixture. To the extent any of the molecules are identified as a marker, the amount of the marker is compared with the amount of the marker from a standard to determine if there is a difference Markers also may be detected and/or quantified by methods that do not require physical separation of the markers themselves. For example, nuclear magnetic resonance (NMR) spectroscopy may be used to resolve a profile of a marker from a complex mixture of molecules. An analogous use of NMR to classify tumors is disclosed in Hagberg, NMR Biomed. 11: 148-56 (1998), for example. Additional procedures include nucleic acid amplification technologies, which may be used to determine a marker profile without physical separation of individual molecules. (See Stordeur et al., J. Immunol. Methods 259: 55-64 (2002) and Tan et al., Proc. Nat'l Acad. Sci. USA 99: 11387-11392 (2002), for example.)

A marker in a sample also may be detected and/or quantified, for example, by combining the marker with a binding moiety capable of specifically binding the marker. The binding moiety may include, for example, a member of a ligand-receptor pair, i.e., a pair of molecules capable of having a specific binding interaction. The binding moiety may also include, for example, a member of a specific binding pair, such as antibody-antigen, enzyme-substrate, nucleic acid-nucleic acid, protein-nucleic acid, protein-protein, or other specific binding pairs known in the art. Binding proteins may be designed which have enhanced affinity for a target. Optionally, the binding moiety may be linked with a detectable label, such as an enzymatic, fluorescent, radioactive, phosphorescent or colored particle label. The labeled complex may be detected, e.g., visually or with the aid of a spectrophotometer or other detector, and/or may be quantified.

A marker also may be detected and/or quantified using gel electrophoresis techniques available in the art. In two-dimensional gel electrophoresis, molecules are separated first in a pH gradient gel according to their isoelectric point. The resulting gel then is placed on a second polyacrylamide gel, and the molecules separated according to molecular weight (See, for example, O'Farrell *J. Biol. Chem.* 250: 4007-4021 (1975)). A marker for coronary artery disease may be detected by first isolating molecules from a sample obtained from an individual suspected of having coronary artery disease and then separating the molecules by two-dimensional gel electrophoresis to produce a characteristic two-dimensional gel electrophoresis pattern. The pattern may then be compared with a standard gel pattern produced by separating, under the same or similar conditions, molecules isolated from the standard (e.g., healthy or coronary artery disease subjects). The standard gel pattern may be stored in, and retrieved from, an electronic database of electrophoresis patterns. Thus, it is determined if the amount of the marker in the patient is different from the amount in the standard. The presence of a plurality, e.g., two to fifteen, coronary artery disease markers on the two-dimensional gel in an amount different than a known normal standard indicates a positive screen for coronary artery disease in the individual. The assay thus permits the detection and treatment of coronary artery disease.

A marker also may be detected and/or quantified using any of a wide range of immunoassay techniques available in the art. For example, sandwich immunoassay format may be used to detect and/or quantify a marker in a sample from a patient. Alternatively, conventional immuno-histochemical procedures may be used for detecting and/or quantifying the presence of a marker in a sample using one or more labeled binding proteins.

In a sandwich immunoassay, two antibodies capable of binding a marker generally are used, e.g., one immobilized onto a solid support, and one free in solution and labeled with a detectable chemical compound. Examples of chemical labels that may be used for the second antibody include radioisotopes, fluorescent compounds, and enzymes or other molecules that generate colored or electrochemically active products when exposed to a reactant or enzyme substrate. When a sample containing the marker is placed in this system, the marker binds to both the immobilized antibody and the labeled antibody, to form a "sandwich" immune complex on the support's surface. The complexed marker is detected by washing away non-bound sample components and excess labeled antibody, and measuring the amount of labeled antibody complexed to the marker on the support's surface. Alternatively, the antibody free in solution, which can be labeled with a chemical moiety, for example, a hapten, may be detected by a third antibody labeled with a detectable moiety which binds the free antibody or, for example, the hapten coupled thereto.

Both the sandwich immunoassay and tissue immunohistochemical procedures are highly specific and very sensitive, provided that labels with good limits of detection are used. A detailed review of immunological assay design, theory and protocols can be found in numerous texts in the art, including Butt, W. R., *Practical Immunology*, ed. Marcel Dekker, New York (1984) and Harlow et al. *Antibodies, A Laboratory Approach*, ed. Cold Spring Harbor Laboratory (1988).

In general, immunoassay design considerations include preparation of antibodies (e.g., monoclonal or polyclonal antibodies) having sufficiently high binding specificity for the target to form a complex that can be distinguished reliably from products of nonspecific interactions. As used herein, the term "antibody" is understood to mean binding proteins, for example, antibodies or other proteins comprising an immunoglobulin variable region-like binding domain, having the appropriate binding affinities and specificities for the target. The higher the antibody binding specificity, the lower the target concentration that can be detected. As used herein, the terms "specific binding" or "binding specifically" are understood to mean that the binding moiety, for example, a binding protein, has a binding affinity for the target of greater than about $10^5$ $M^{-1}$, more preferably greater than about $10^7$ $M^{-1}$.

Antibodies to an isolated target marker which are useful in assays for detecting a coronary artery disease in an individual may be generated using standard immunological procedures well known and described in the art. See, for example *Practical Immunology*, supra. Briefly, an isolated marker is used to raise antibodies in a xenogeneic host, such as a mouse, goat or other suitable mammal. The marker is combined with a suitable adjuvant capable of enhancing antibody production in the host, and is injected into the host, for example, by intraperitoneal administration. Any adjuvant suitable for stimulating the host's immune response may be used. A commonly used adjuvant is Freund's complete adjuvant (an emulsion comprising killed and dried microbial cells and available from, for example, Calbiochem Corp., San Diego, or Gibco, Grand Island, N.Y.). Where multiple antigen injections are desired, the subsequent injections may comprise the antigen in combination with an incomplete adjuvant (e.g., cell-free emulsion). Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target and have the desired binding affinity.

Antibody binding domains also may be produced biosynthetically and the amino acid sequence of the binding domain manipulated to enhance binding affinity with a preferred epitope on the target. Specific antibody methodologies are well understood and described in the literature. A more detailed description of their preparation can be found, for example, in *Practical Immunology*, (supra).

In addition, genetically engineered biosynthetic antibody binding sites, also known in the art as BABS or sFv's, may be used to determine if a sample contains a marker. Methods for making and using BABS comprising (i) non-covalently associated or disulfide bonded synthetic $V_H$ and $V_L$ dimers, (ii) covalently linked $V_H$-$V_L$ single chain binding sites, (iii) individual $V_H$ or $V_L$ domains, or (iv) single chain antibody binding sites are disclosed, for example, in U.S. Pat. Nos. 5,091,513; 5,132,405; 4,704,692; and 4,946,778. Furthermore, BABS having requisite specificity for the marker can be derived by phage antibody cloning from combinatorial gene libraries (see, for example, Clackson et al. *Nature* 352: 624-628 (1991)). Briefly, phages, each expressing on their coat surfaces BABS having immunoglobulin variable regions encoded by variable region gene sequences derived from mice pre-immunized with an isolated marker, or a fragment thereof, are screened for binding activity against the immobilized marker. Phages which bind to the immobilized marker are harvested and the gene encoding the BABS is sequenced. The resulting nucleic acid sequences encoding the BABS of interest then may be expressed in conventional expression systems to produce the BABS protein.

An isolated marker also may be used for the development of diagnostic and other tissue evaluating kits and assays to monitor the level of the marker in a tissue or fluid sample. For example, the kit may include antibodies or other specific binding proteins which bind specifically to one or more markers and which permit the presence and/or amount of the one or more markers to be detected and/or quantified in a tissue or fluid sample.

Suitable kits for detecting one or more markers are contemplated to include, but are not limited to, a receptacle or other means for capturing a sample to be evaluated and a means for detecting the presence and/or amount in the sample of one or more of the markers described herein. Means for detecting in one embodiment includes, but is not limited to, one or more antibodies specific for these markers and means for detecting the binding of the antibodies to these markers by, for example, a standard sandwich immunoassay as described herein. Where the presence of a marker located within a cell is to be detected (e.g., as from a tissue sample) the kit also may comprise means for disrupting the cell structure so as to expose intracellular components.

The markers of the invention may include nucleic acids of a particular sequence. One or more of the markers may be detected and/or quantified by determining an amount of the marker nucleic acid in a sample, using, for example, Real-Time Quantitative PCR (RT-PCR) and comparing the measured amount to a standard. RT-PCR effectively measures the amount of a marker nucleic acid resulting from PCR. A positive result represents a measured amount of the marker nucleic acid that is different than the amount of the marker from a standard.

Primers can be developed that are complementary to the nucleic acid sequence of a particular nucleic acid marker. These primers direct a polymerase to copy and amplify that particular nucleic acid. RT-PCR detects the accumulation of the amplified nucleic acid marker during the reaction. During the exponential phase of the PCR reaction, the accumulating nucleic acid marker is measured. A calibration standard having a known concentration of nucleic acid is used to prepare a standard curve from which the quantity of the nucleic acid marker in the tested sample is extrapolated.

Once the amount of a nucleic acid marker in a sample is known, it can be compared to the amount of the marker from a standard. The standard for classification of coronary artery disease patients can be determined by empirical means. For example, the amount can be determined by amplifying the nucleic acid marker in a sample from a population of one or more known normal individuals and quantitatively analyzing the amount of a nucleic acid marker in the population.

Also, additional forms of chemical analysis of a sample can be performed. For example, quantitative tests can be carried out that indicate the amounts of each marker in a sample. A colorimetric assay is a quantitative chemical analysis measuring color intensity produced by reacting a sample with a reactant as a proxy for the amount of the assayed material in a sample. Reagents can be provided that, when reacted with any marker, produce a color in the assay sample. The intensity of that color is dependent on the amount of the marker in the sample. By comparison of the intensity with a calibrated color card and/or standard, the amount of the marker in the sample can be determined. This amount can then be compared with the amount of the marker from a standard (such as from a known normal person).

Additionally, urinalysis can be used to determine the amount of a marker in a urine sample. Urine samples are tested with a variety of different instruments and techniques. Some tests use dipsticks, which are thin strips of plastic that change color in the presence of specific substances. Dipsticks could be used to measure the amount of a marker.

Not only does comparing the level of each of at least two markers to the level of each of the two markers from a standard allow for diagnosis of having or being at risk of having coronary artery disease, but this same comparison methodology can be adapted to other uses. For example, the markers could be used to screen candidate drugs for treating coronary artery disease. In this instance, treatment with candidate drugs would be monitored by monitoring the level of the markers. To the extent the markers returned to the standard level from the diseased level, efficacy could be determined. Moreover, with any drug that has already been found effective to treat coronary artery disease, it may be that certain patients may be responders and some may be non-responders. Accordingly, the markers could be monitored during treatment to determine if the drug is effective by determining if the level of the markers return to the standard level. Of course, there may not be any existing, known population of responders and non-responders, so that the efficacy of drug treatment on any coronary artery disease patient can be monitored over time. To the extent it is not efficacious, its use can be discontinued and another drug supplied in its place.

Moreover, comparing the level of each of at least two markers to the level of each of two markers from a standard can be done as a preventative screening measure and not just when cognitive deficit is observed (i.e., after the disease may have progressed). For example, assuming no evidence of cognitive decline, patients could be monitored after a certain age and at predetermined intervals in order to obtain a diagnosis of having or being at risk of having coronary artery disease at the earliest possible time. To the extent the screen is positive, a medical professional might recommend further monitoring for disease progression (either monitoring according to the invention or cognitive monitoring), and/or the medical professional might begin treatments with a drug or other therapy.

Moreover, the markers can be used to validate animal models of coronary artery disease. For example, in any particular model, a sample could be analyzed to determine if levels of the markers in the animal are the same as the levels of the markers in a known coronary artery disease patient. This would validate the model, for example, to test candidate drugs in the manner described above.

Example 1

This example describes the methodology used to identify markers for coronary artery disease. Briefly, eighty (80) male subjects were included in the study and underwent coronary angiography. A classification of the subjects into either diseased or control categories was achieved using the Coronary Artery Disease Prognostic Index [Mark D B, Nelson C L, Califf R M, et al. Continuing evolution of therapy for coronary artery disease. Initial results from the era of coronary angioplasty. Circulation. 1994; 89: 2015-2025]. The Coronary Artery Disease Prognostic Index is an ordinal scale with values ranging from zero to one-hundred and is a measure of the degree of coronary arterial stenosis; this index considers not only the number of diseased vessels but also any significant involvement of the left anterior descending coronary artery, particularly when there is involvement of the proximal segment and/or when proximal segment stenosis is severe. Forty (40) subjects were determined to have a Coronary Artery Disease Prognostic Index (or 'CAD Index') equal to zero (mean age of 51.6 years), and forty (40) subjects were determined to have a CAD Index greater than zero (mean age 53.4 years). A plasma sample was also acquired from each subject at the time of the coronary angiography. Bioanalytical analyses were conducted on plasma of these subjects. As a result, unique spectral peaks that characterize molecules were generated. Following data manipulation and statistical analysis, a subset of these peaks was identified that could classify subjects as having CAD Index equal to zero, or CAD Index greater than zero, with varying degrees of sensitivity. The molecules characterized by this subset of peaks were then designated as the markers of interest. Ultimately, a group of fifteen markers were shown to achieve the best specificity and sensitivity.

Two-hundred and fifty (250) microliters of plasma was collected from each subject using citrate as the anti-coagulant during blood drawing. Two samples had problems during sample preparation and were excluded from the analyses. The total number of samples analyzed was thus seventy-eight (78). Plasma samples were analyzed using four (4) methodologies. The spectral peaks were generated as follows.

(A) Liquid Chromatography ("LC") Tandem Mass Spectrometry ("LC/MS") Profiling of Lipids.

This method utilizes liquid chromatography and mass spectrometry conditions that are optimized for resolution and detection of lipid molecules.

Protocol Summary:
  Lipids are extracted from plasma using isopropanol
  The extract is centrifuged to remove precipitated proteins
  The supernatant is injected directly into LC/MS system
  LC: reversed-phase HPLC (Waters 600-MS pump with Waters 717 autosampler)
  MS: ThermoFinnigan XSQ 700/7000 Quantum
  MS are spectra acquired in the positive ion mode over m/z 300-1900

Plasma samples were prepared for lipid analysis by adding 0.6 mL of isopropanol to 150 microliters of whole plasma followed by centrifugation to precipitate and remove proteins. To prepare samples for LC/MS analysis, 400 microliters of water were added to 100 microliter of the supernatant and 200 microliters of this mixture was transferred to an autosampler for subsequent LC/MS analysis. A ThermoFinnigan XSQ 700/7000 (ThermoFinnigan, San Jose Calif.) was used to acquire plasma lipid LC/MS spectra. The LC component consisted of a Waters 717 series autosampler and a 600 series single gradient forming pump (Waters Corporation, Milford, Mass.). Samples were injected onto an Inertsil column from (ODS 3, 5 µM, 3 mm×100 mm) protected by an R2 guard column (Chrompack). A 75 µL aliquot of mouse plasma extract was injected twice in a random order. The random sequence was applied to prevent detrimental effects of possible drift during analysis on the results obtained from multivariate statistics. The elution gradient was formed by using three mobile phases: A (water/acetonitrile/ammonium acetate (1M/L)/formic acid, 93.9:5:1:0.1, vol/vol/vol/vol), B (acetonitrile/isopropanol/ammonium acetate, (1M/L)/formic acid, 68.9:30:1:01, vol/vol/vol/vol), C (isopropanol/dichloromethane/ammonium acetate (1M/L)/formic acid, 48.9:50:1:0.1, vol/vol/vol/vol). The samples were fractionated at 0.7 mL/min by a four-step gradient; (1) over 15 min going from 30% to 95% buffer B; (2) 20 min gradient from 95% to 35% B and 60% C with a 5 min hold at this step; (3) rapid one min gradient of 35% B and 60% C going to 95 and 0% respectively; (4) 95% buffer B going back to 30% over 5 min period.

The electrospray ionization voltage was set to 4.0 kV and the heated transfer capillary to 250° C. Nitrogen sheath and auxiliary gas settings were 70 and 15 units, respectively. For quantification of metabolites, the scan cycle consisted of a single full scan (1 s/scan) mass spectrum acquired over m/z 200-1700 in the positive ion mode.

(B) LC/MS Profiling of Amino Acids and Polar Metabolites

Protocol Summary:
  Metabolites are extracted from plasma using methanol
  The extract is centrifuged to remove precipitated proteins
  The supernatant is derivatized using butanolic HCl
    Butylation blocks carboxylic acid groups and enhances protonation for MS analysis
  The supernatant is dried and reconstituted for injection into the LC/MS system
  LC: reversed-phase HPLC (Waters Alliance 2690)
  MS: ThermoFinnigan LCQ
  Spectra acquired in the positive ion mode over m/z 50-1000

The spectral peaks for LC/MS profiling of amino acids and polar metabolites were generated as follows. An LC/MS analysis was performed using a high performance liquid chromatography system ("HPLCS") (an Alliance Waters 2690 separation module available from Waters Corp. of Milford, Mass.) and a mass spectrometry system comprising an electrospray ion source and a quadruple ion trap detector (an LCQ ion trap mass spectrometer available from ThermoFinnigan of San Jose, Calif.).

The following mixtures and reagents were prepared. Three "stock solutions" were prepared. As a chromatographic calibration internal standard ('IS'), one (1) mg d5-phenylalanine was added to 1 ml dimineralised water; 1 mg d3-gutamate was added to 1 ml dimineralised water; and 1 mg d3-leucine was added to 1 ml dimineralised water. An "IS-stock solution" was prepared by adding 100 µl of each of the 1 mg/ml stock solutions to 700 µl water (final concentration of 100 µg/ml). An "IS-work solution" was prepared by diluting 100 µl of the IS-stock solution to 1 ml with 900 µl of dimineralized water (final concentration of 10 µg/ml). "Solution A" was 300 mg/ml dithiothreitol (DTT). "Solution B" was Butanolis hydrochloric acid (prepared by adding 5 ml of 37% HCl (12N) to 15 ml of n-butanol). "Solution C" was 0.1% Formic acid and 1 mg/ml DTT in dimineralised water (prepared by adding 100 µl formic acid and 35 µl solution A to 100 ml dimineralised water). Endogenous metabolites were extracted from plasma samples and derivated using butanolic hydrochloric acid (solution B). Butylation was performed in order to block the carboxylic acid function of the amino acids and enhance the formation of protonated molecules, thereby increasing MS sensitivity. Three deuterated amino acids were added as an internal standard for quality control and scaling calculations. More specifically, the sample was prepared by first adding 10 µl of plasma into a small vial with 10 µl of the IS-work solution and then vortexing briefly. Next, 10 µl of solution A was added to the vial, and the mixture was incubated for at least 30 minutes at room temperature. 100 µl of methanol (high-purity grade) was then added, and the mixture was centrifuged at 3500 relative centrifugal force ("rcf") for 5 minutes. The supernatant was collected and dried down under dry nitrogen. Next, 100 µl of solution B was added to the dried supernatant and vortexed briefly. The samples were next sealed and placed in an air oven and incubated at 65° for at least 60 minutes. The seal was then removed, and the excess HCL-butanol was evaporated to dryness under dry nitrogen. The derivative was then reconstituted in 100 µl of solution C. The sample was then analyzed using LC/MS. The analysis was done using an HPLCS. The HPLCS included a stationary phase and a mobile phase. The stationary phase included a column and a guard column. The column used was a reverse-phase $C_{18}$ chromatography column having an inner diameter of 3 mm and a length of 100 mm and including octadecyl-bonded silica particles with a mean diameter of 5 µm (a Chrompack Inertsil® 5 μm ODS-3 100×3 mm from GL Sciences, Inc. of Japan). The guard column used was a $C_{18}$ guard column having an inner diameter of 10 mm and a length of 50 mm and including octadecyl-bonded silica particles with a mean diameter of 5 μm (a Chrompack Inertsil® 5 μm ODS-3 (S2) from GL Sciences, Inc. of Japan). The HPLCS also included an autosampler. The mobile phase included two solvents (Solvent A and Solvent B). Solvent A was a 0.1% formic acid solution made by adding 1 ml formic acid to 1000 ml water and then mixing and degassing the solution by ultra-sonication for 5 minutes. Solvent B was 80% acetonitrile (high-purity grade) in 0.1% formic acid solution that was made by mixing 800 ml acetonitrile, 1000 ml water and 1 ml formic acid, and degassing by ultra-sonication for 5 minutes. The column temperature was kept at ambient temperature and the temperature of the autosampler was 10° C. The mobile phase passed through the column at a rate of 0.3 milliliters per minute. The elution gradient for the HPLCS was performed as illustrated in the Table below. The injection volume was 10 μl of the prepared sample.

TABLE

Elution gradient of HPLCS.

| Time (min.) | Flow (ml/min.) | Solvent A (%) | Solvent B (%) |
|---|---|---|---|
| 0.00 | 0.3 | 100 | 0 |
| 2.50 | 0.3 | 95 | 5 |
| 20.00 | 0.3 | 60 | 40 |
| 22.00 | 0.3 | 0 | 100 |
| 30.00 | 0.3 | 0 | 100 |
| 30.01 | 0.3 | 100 | 0 |
| 35.00 | 0.3 | 100 | 0 |

The mass-to-charge ratio of the eluting metabolites was determined using a mass spectrometry system including an electrospray ion source (ESI) and a quadruple ion detector scanning in the positive ion mode. The electrospray ionization voltage was set to about 3.0 to about 4.0 kV and the heated transfer capillary to 250° C. Nitrogen sheath and auxiliary gas settings were 70 and 5 units, respectively. For quantification of metabolites, the scan cycle consisted of a two full scan (1 s/scan) mass spectrum acquired over m/z 105-1000 in the positive ion mode. The max injection time was 300 ms, and the source ionization was about 5.0 kV. The apparatus was tuned on a mixture of butylated amino acids (e.g., Phe, Pro, Trp).

(C) Proton Nuclear Magnetic Resonance ("NMR") spectroscopy

NMR analysis requires minimal sample preparation and is a very reproducible technique. Also advantageous is that there is no requirement for pre-selection of the metabolites of interest or postulation of the metabolites affecting a disease process. Thus, a wide range of low molecular weight metabolites and macromolecules can be monitored in a short period of time (a spectrum can be acquired in <10 minutes), without prior knowledge or expectation of the results. In addition, NMR is non-invasive, non-destructive and non-equilibrium perturbing; and the data provide qualitative structural information.

NMR pulse sequences are available for filtering signals from either high or low molecular weight components. The use of two different pulse sequences, optimized for both low and high molecular weight compounds, provides the opportunity to gain much more information than the use of a single, standard pulse sequence (which is optimized for neither). The type of data acquisition employed in this study is Carr-Purcell-Meiboom-Gill spin echo NMR ("CPMG NMR"). CPMG NMR is optimized for the measurement of signals from low molecular weight and non-protein bound metabolites. The CPMG pulse sequence removes signals of protons that have fast transverse relaxation times (short T2) and give rise to broad peaks. Such protons are typically associated with large proteins and lipoprotein components.

Protocol Summary:
  Plasma is diluted in buffer (minimal preparation) and measured directly
  $^1$H-NMR spectra are acquired using the CPMG spin-echo NMR pulse sequence and a Bruker AVANCE 600 MHz NMR spectrometer
  Following Fourier transformation, phase correction, and baseline correction, spectral intensities are measured via either peak-picking or "bucketing"
  For data that has been peak-picked, the Partial Linear Fit™ (PLF™) algorithm is used to align peaks and compensate for minor changes in chemical shift.

The plasma samples were prepared by adding 0.6 mL of isopropanol to 150 μL of whole plasma followed by centrifugation to precipitate and remove proteins. A 500 μL aliquot of the supernatant was concentrated to dryness and redissolved in 750 μL of MeOD prior to NMR analysis. NMR spectra were recorded in triplicate in a fully automated manner on a Bruker AVANCE 600 MHz spectrometer using a proton NMR set-up operating at a temperature of 293 K. Free induction decays (FIDs) were collected as 64K data points with a spectral width of 8.000 Hz; 45 degree pulses were used with an acquisition time of 4.10 s and a relaxation delay of 2 s. The spectra were acquired by accumulation of 512 FIDs. The spectra were processed using the standard Varian software. An exponential window function with a line broadening of 0.5 Hz and a manual baseline correction was applied to all spectra. After referring to the —$CD_3$ signal of $CD_3OD$ ($\delta$=3.30), line listings were prepared using the standard Bruker NMR software. To obtain these listings all lines in the spectra above a threshold corresponding to about three times the signal-to-noise ratio were collected and converted to a data file suitable for statistical analysis.

(D) Gas chromatography tandem mass spectrometry (GC/MS) profiling

GC has the advantage of high separation efficiency and robust retention times combined with sensitive and selective (electron impact) mass detection. However, many compounds contain polar functional groups that are either thermally labile at the temperatures required for their separation or are not volatile at all. In addition the peak shape of compounds with polar functional groups can be unsatisfactory because of undesired column interaction such as irreversible adsorption. In order to address these issues, derivatization of the compounds prior to GC analysis is necessary.

BG Protocol Summary:
  Metabolites are extracted from plasma using methanol
  The extract is centrifuged to remove precipitated proteins
  The supernatant is derivatized by first oximation and subsequently silylation
  After derivatization the sample is analyzed by GC-MS using a non-polar analytical column, and the analytes are separated in order of their boiling point
  autosampler: ATAS Focus
  GC: Agilent 6890 N with PTV (programmed temperature vaporizer) injector
  MS: Agilent 5973 Mass Selective Detector
  Mass spectrometric detection is achieved using electron impact ionization and full scan monitoring mode Prior to statistical analysis, all spectral peaks, were aligned and normalized in order to allow for quantitative comparison across all subject samples. This alignment and normalization was done separately for each four measurement methodologies described above (LC/MS of lipids, LC/MS of polar metabolites and amino acids, GC/MS, and NMR). Alignment was achieved using software to adjust for minor differences in spectral peaks arising from variation in analyte chromatographic retention times. Subsequent spectral peak normalization was accomplished by determining a proper scaling factor for each data set, typically through the use of internal standards.

After the steps of alignment and normalization, the data consisted of sample-specific files of spectral peaks which are identified by their mass-to-charge ratio and retention time in the case of LC/MS and GC/MS, and by their chemical shift in the case of NMR. After normalization, the intensities of these spectral peaks are directly comparable across all subject samples. The spectral data also were subjected to a number of pre-processing steps. For example, based on signal-to-noise criteria, the data were filtered to exclude peaks not satisfying a defined threshold intensity value. Further, peaks which resisted satisfactory alignment across data sets were also excluded from consideration. FIG. 2a and FIG. 2b illustrate the steps of data pre-processing for the LC/MS and GC/MS, and NMR data sets, respectively.

Figure 2C:
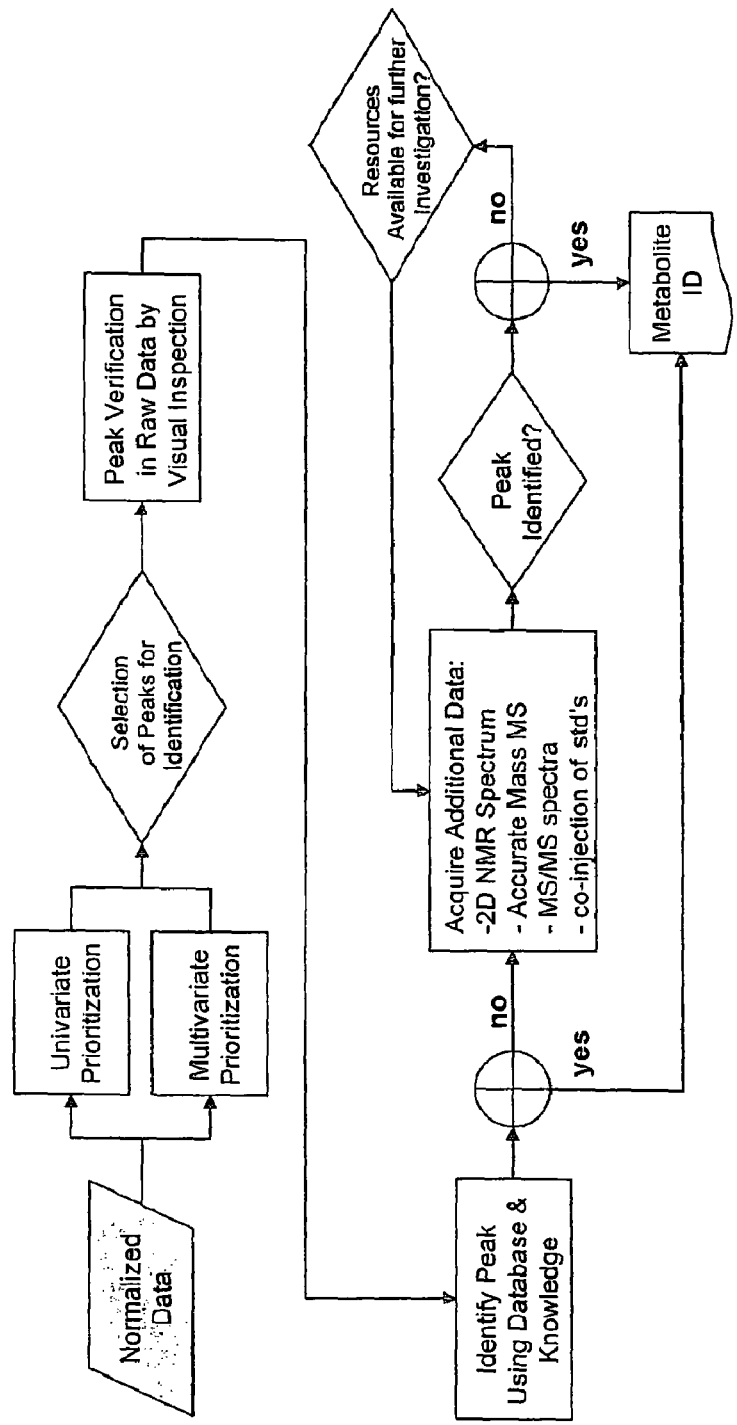
FIG. 2c shows a workflow for identifying analytes from spectral peaks.

The biochemical analytes in plasma which gave rise to the spectral peaks in the data sets were determined using tandem mass spectrometry for LC/MS and GC/MS, and 2-dimensional NMR for spectral peaks from the NMR platform. The characteristics of each peak, such as mass, chromatographic retention time, 2-dimensional NMR spectra, tandem mass spectrometric spectra and the like, were compared to a database of previously observed and identified peaks and analytes. The general workflow for peak identification is shown in FIG. 2c. This identification exercise resulted in ninety-four (94) identified analytes; these are listed in Table 1, together with the method by which the analyte peak signal was identified. In Table 1, "2D NMR" indicates a match of the 2-dimensional NMR spectrum to a reference spectrum in a database, "MS/MS" indicates a match of a tandem mass spectrometry mass spectrum to a reference spectrum in a database, "full scan m/z match" indicates a match of the analyte mass-to-charge ratio and chromatographic retention time to a reference database of analyte mass-to-charge ratio and chromatographic retention times, "chemical shift match" indicates a match of an NMR chemical shift to a reference database of analyte chemical shifts, "TNO database" indicates a match of a tandem mass spectrometry mass spectrum to a reference spectrum in a database, and "NIST library" indicates a match of a mass spectrometry mass spectrum to a reference spectrum in a United States National Institute of Standards and Technology database. Additional abbreviations used in Table 1 are as follows: "PC", Phosphatidylcholine; "LPC", Lysophosphatidylcholine; "TG", Triglyceride; "SPM", Sphingomyelin; "CE", Cholesteryl ester. Further, the nomenclature CX:Y indicates, for a molecule of SPM, TG, CE or LPC, X number of total carbon atoms in the fatty acid portion(s) of the molecule, and Y number of double-bonds in the fatty acid portion(s) of the molecule. The analyte identified as "C18:2 (fatty acid)" is the fatty acid molecule with scientific name 9,12-Octadecadienoic Acid and common name Linoleic Acid.

Table 1 includes analytes which were represented by multiple peaks in the bioanalytical platform; hence there are instances of one analyte identification appearing multiple times in Table 1.

Univariate Statistical Analysis

Figure 3:
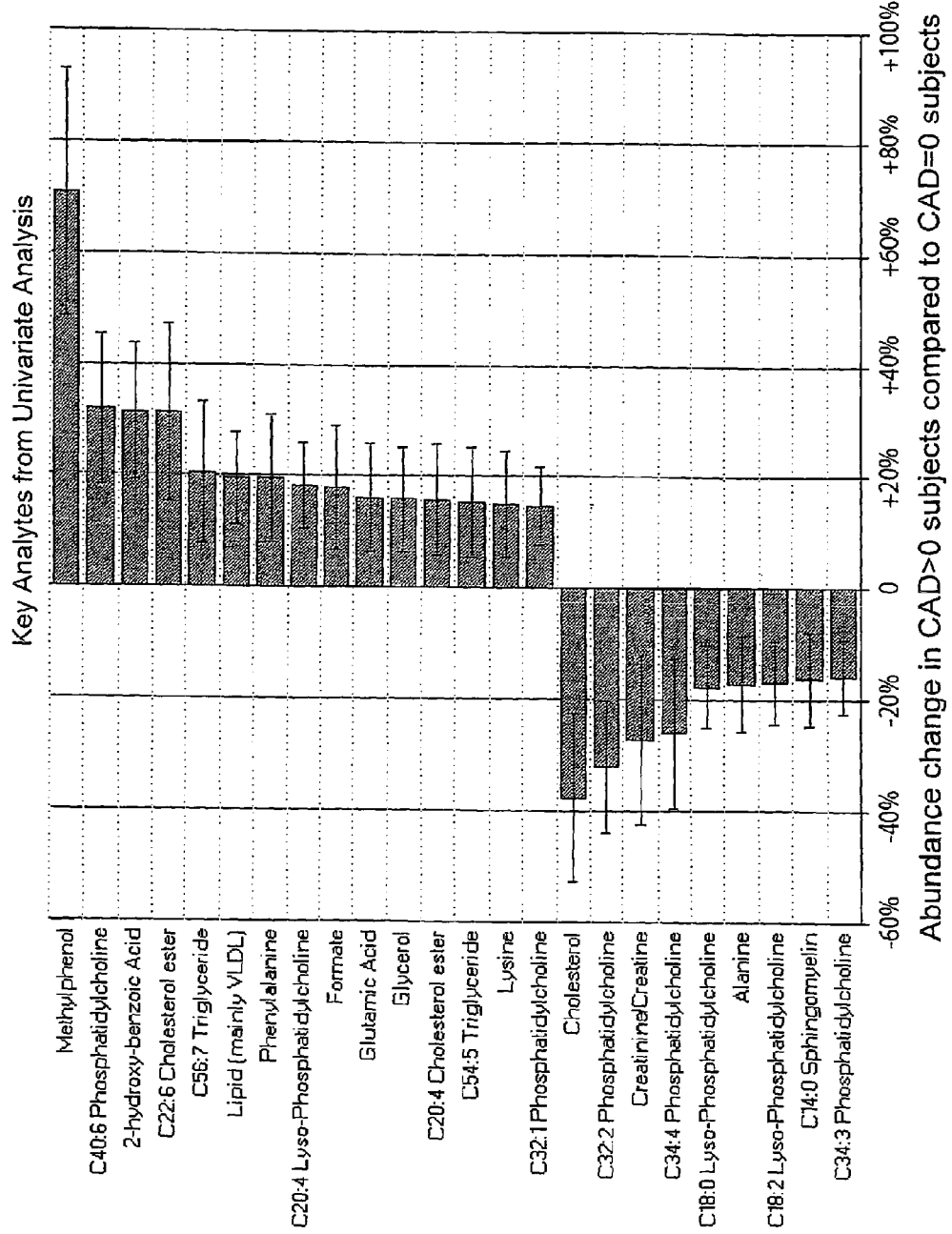
FIG. 3 is an exemplary plot of the difference in analyte levels between subjects with coronary artery disease and subjects with no coronary artery disease.

Table 1 also shows the results of a univariate statistical analysis of the mean levels of each analyte between the two groups (CAD Index equal to zero and CAD Index greater than zero), and a corresponding p-value. Specifically, a homoscedastic t-test was performed and the corresponding p-value is reported in Table 1. Also shown in Table 1 is, for each analyte, the ratio of the level of that analyte in the CAD Index greater than zero group to the CAD Index equal to zero group, denoted as "DIS/CTRL ratio". FIG. 3 is a graphical representation of a subset of the results in Table 1.

TABLE 1

| Analyte | Mode of Identification | DIS/CTRL ratio | p-value |
|---|---|---|---|
| 2-hydroxy-benzoic acid | NIST library | 0.76 | 0.0028 |
| 3-D-Hydroxybutyrate | TNO database | 0.97 | 0.5183 |
| Alanine | 2D NMR | 1.21 | 0.0033 |
| C14:0 SPM | MS/MS | 1.19 | 0.0054 |
| C16:0 LPC | full scan m/z match | 1.03 | 0.3738 |
| C16:0 SPM | MS/MS | 1.06 | 0.0359 |
| C16:1 CE | MS/MS | 1.06 | 0.5849 |
| C18:0 LPC | MS/MS | 1.21 | 0.0006 |
| C18:1 CE | MS/MS | 1.02 | 0.5356 |
| C18:2 (Linoleic Acid) | spectrum match to DB | 1.20 | 0.0009 |
| C18:2 CE | MS/MS | 1.02 | 0.7128 |
| C18:2 LPC | full scan m/z match | 1.13 | 0.0330 |
| C18:3 CE | MS/MS | 1.11 | 0.0613 |
| C18:3 LPC | MS/MS | 1.05 | 0.0657 |
| C20:4 CE | full scan m/z match | 0.86 | 0.0397 |
| C20:4 LPC | full scan m/z match | 0.85 | 0.0026 |
| C20:5 CE | full scan m/z match | 0.85 | 0.4046 |
| C21:0 SPM | MS/MS | 1.17 | 0.0098 |
| C22:0 SPM | MS/MS | 1.14 | 0.0046 |
| C22:6 CE | MS/MS | 0.76 | 0.0197 |
| C22:6 LPC | full scan m/z match | 0.87 | 0.1538 |
| C23:0 SPM | MS/MS | 1.17 | 0.0034 |
| C24:0 SPM | MS/MS | 1.15 | 0.0071 |
| C26:0 PC | full scan m/z match | 1.25 | 0.0052 |
| C32:0 PC | MS/MS | 1.04 | 0.3611 |
| C32:1 PC | MS/MS | 0.87 | 0.0076 |
| C32:2 PC | MS/MS | 1.47 | 0.0000 |
| C34:1 PC | full scan m/z match | 1.06 | 0.2156 |
| C34:2 PC | MS/MS | 1.09 | 0.0001 |
| C34:3 PC | MS/MS | 1.19 | 0.0006 |
| C34:4 PC | full scan m/z match | 1.37 | 0.0040 |
| C36:1 PC | MS/MS | 1.10 | 0.0889 |
| C36:2 PC | MS/MS | 1.10 | 0.0002 |
| C36:3 PC | MS/MS | 1.11 | 0.0004 |
| C36:4 PC | full scan m/z match | 1.00 | 0.9542 |
| C36:5 PC | MS/MS | 0.98 | 0.9201 |
| C38:2 PC | MS/MS | 1.05 | 0.2944 |
| C38:4 PC | full scan m/z match | 0.96 | 0.2686 |
| C38:5 PC | full scan m/z match | 0.97 | 0.6147 |
| C38:6 PC | full scan m/z match | 0.90 | 0.1953 |
| C40:6 PC | MS/MS | 0.76 | 0.0069 |
| C46:0 TG | MS/MS | 1.13 | 0.0274 |
| C46:1 TG | MS/MS | 1.22 | 0.3563 |
| C48:1 TG | MS/MS | 1.10 | 0.6184 |
| C48:2 TG | MS/MS | 1.14 | 0.3787 |
| C48:3 TG | MS/MS | 1.15 | 0.3418 |
| C50:1 TG | MS/MS | 1.03 | 0.8661 |
| C50:2 TG | MS/MS | 1.02 | 0.8697 |
| C50:3 TG | MS/MS | 1.03 | 0.6854 |
| C50:4 TG | MS/MS | 1.06 | 0.5760 |
| C52:1 TG | MS/MS | 0.94 | 0.6667 |
| C52:2 TG | MS/MS | 0.93 | 0.2886 |
| C52:3 TG | MS/MS | 0.95 | 0.4087 |
| C52:4 TG | MS/MS | 0.94 | 0.2340 |
| C52:5 TG | MS/MS | 0.94 | 0.4036 |
| C54:1 TG | MS/MS | 0.93 | 0.6300 |
| C54:2 TG | MS/MS | 0.89 | 0.2698 |
| C54:3 TG | MS/MS | 0.88 | 0.0809 |
| C54:4 TG | MS/MS | 0.87 | 0.0551 |
| C54:5 TG | MS/MS | 0.87 | 0.0429 |
| C54:6 TG | MS/MS | 0.85 | 0.0572 |
| C54:7 TG | full scan m/z match | 0.84 | 0.1751 |

TABLE 1-continued

| Analyte | Mode of Identification | DIS/CTRL ratio | p-value |
|---|---|---|---|
| C56:7 TG | full scan m/z match | 0.83 | 0.0425 |
| C56:8 TG | full scan m/z match | 0.80 | 0.1180 |
| Cholesterol | 2D-NMR | 1.60 | 0.0007 |
| Choline | 2D-NMR | 1.02 | 0.7685 |
| Creatinine/Creatine | 2D NMR | 1.37 | 0.0087 |
| Formate | chemical shift match | 0.85 | 0.0451 |
| Glucose | 2D NMR | 1.06 | 0.3752 |
| glutamic acid | TNO database | 0.86 | 0.0321 |
| Glycerol | chemical shift match | 0.86 | 0.0353 |
| glycerol | TNO database | 1.07 | 0.4608 |
| glycine | TNO database | 0.98 | 0.8227 |
| hexadecanoic acid | NIST library | 1.16 | 0.0141 |
| histidine | TNO database | 0.88 | 0.0212 |
| Isoleucine | chemical shift match | 1.11 | 0.0409 |
| isoleucine | TNO database | 0.92 | 0.0959 |
| lactic acid | TNO database | 0.88 | 0.0783 |
| Lipid | 2D-NMR | 1.07 | 0.2220 |
| Lipid (mainly LDL) | 2D NMR | 0.89 | 0.0059 |
| Lipid (mainly VLDL) | 2D NMR | 0.84 | 0.0031 |
| lysine | TNO database | 0.87 | 0.0420 |
| methylphenol | NIST library | 0.59 | 0.0017 |
| oleic acid | NIST library | 1.14 | 0.0679 |
| Phenylalanine | chemical shift match | 0.84 | 0.0334 |
| phenylalanine | TNO database | 0.95 | 0.0806 |
| 5-oxo-L-proline | spectrum match to DB | 0.90 | 0.0378 |
| Proline | 2D-NMR | 0.87 | 0.0520 |
| proline | TNO database | 0.96 | 0.6101 |
| tryptophan | TNO database | 0.90 | 0.0650 |
| tyrosine | 2D NMR | 0.90 | 0.2305 |
| uric acid | TNO database | 0.88 | 0.1637 |
| Valine | chemical shift match | 1.16 | 0.0179 |

Multivariate Statistical Analysis: Classification and Recursive Feature Elimination In addition to univariate statistical analysis, multivariate statistical analyses were also performed on these data. In order to determine the minimal optimal subset of analytes which best segregate samples from subjects with CAD Index equal to zero and CAD Index greater than zero, an approach known as Recursive Feature Elimination was used. First, a "classification algorithm" was chosen which accepts as input N components (i.e., N analytes; N=94 in this study, namely, those analytes listed in Table 1), and returns (i) the success of segregating CAD Index equal to zero and CAD Index greater than zero samples (as measured by specificity and sensitivity) achieved by a linear combination of the N components, and (ii) a ranking of the N input components based on their contribution to the classification. Next, all identified analytes from the experiment (aligned, normalized, and pre-processed as discussed above) were allowed as input to the classification algorithm. With these components as inputs, the algorithm was then run to converge upon a linear combination of input components used to classify CAD Index equal to zero and CAD Index greater than zero samples. Next, the ranking criterion ("weight") was recorded for each input analyte. The weights are the coefficients in the linear combination of input components as determined by the algorithm (the final weight is actually a mean weight, averaged over multiple Cross-Validation iterations; see discussion below). The success in classifying CAD Index equal to zero (hereafter referred to as "CAD=0") samples and CAD Index greater than zero (hereafter referred to as "CAD>0") was then computed (i.e., specificity and sensitivity; this is the "Training Performance"). Next, the "Cross-Validation" performance of this combination of analytes in classifying CAD=0 and CAD>0 samples using the Cross-Validation method was computed, as described below. The analyte with the lowest weight was removed. These steps were repeated until only one analyte remained. The minimum number of analytes required to achieve the highest success (i.e., the highest specificity and sensitivity) in segregating CAD Index equal to zero and CAD Index greater than zero samples was then determined; in the present experiment this minimum number of analytes was determined to be fifteen (15). These markers are then a linear combination of analyte levels, the coefficients in the combination being the weights corresponding to each analyte.

Specifically, the process of Recursive Feature Elimination follows the steps as follows:

1. Choose a 'classification algorithm' which accepts as input N components (i.e. N spectral peaks), and returns (i) the success of segregating Control and Disease samples (as measured by specificity and sensitivity) achieved by a linear combination of the N components, and (ii) a ranking of the N input components based on their contribution to the classification.
2. Allow all analytes data (aligned, normalized and pre-processed) as input to the classification algorithm.
3. With these components as inputs, run the algorithm to converge upon a linear combination of input analytes to be used to classify Control and Disease samples.
4. Record the ranking criterion ('weight') for each analyte. The weights are the coefficients in the linear combination of input components as determined by the algorithm (the final weight is actually a mean weight, averaged over multiple Cross-Validation iterations).
5. Compute the 'Cross-Validation' performance of this combination of spectral peaks in classifying Control and Disease samples using the Cross-Validation method (discussed below), as well as the standard error for the cross-validation tests.
6. Remove the analyte with the lowest weight.
7. Repeat Step 3 through Step 6, until only one analyte remains.
8. Determine the minimum number of analytes required to achieve the highest success in segregating Control and Disease samples; this Marker is composed of a linear combination of analyte values, the coefficients in the combination being the weights corresponding to each analyte.

The term "Recursive Feature Elimination" reflects the successive pruning of the list of analytes one by one. FIG. 4 shows the Cross-Validated Performance as a function of number of analytes for CAD Index equal to zero (hereafter referred to as "CAD=0") and CAD Index greater than zero (hereafter referred to as "CAD>0") samples. The algorithm progresses from right to left in the figure, initially considering all ninety-four (94) available analytes and subsequently recursively eliminating inputs until only one analyte remains. The horizontal axis is logarithmic in base two.

The classification algorithms applied to determine the markers is termed a "Logistic Classifier." See J. A. Anderson, *Logisitic Discrimination in Hand Book Statistics*, P. R. Krishnaiah and L. N. Kanal, eds., Vol. 2, pp. 169-191, Amsterdam (1982).

"Cross-Validation Performance" is the classification success of a multivariate marker which has been constructed based on a subset of the available samples, and tested on the remaining samples which have been a priori intentionally left out [Hastie T, Tibshirani R and Friedman J. (2001) "The Elements of Statistical Learning," Springer-Verlag, New York, 2001.] FIG. 5 provides an illustrative overview of this process. A typical situation for the present study is to construct a Marker based only on thirty-four (34) CAD>0 samples and thirty-four (34) CAD=0 samples chosen at random, and to test the performance (classification success) of the resultant Marker in classifying the remaining six (6) CAD>0 and six (6) CAD=0 samples which were excluded. This process is repeated successively many times, with different sets of randomly chosen 6+6 samples 'left out'. The reported 'Cross-Validation Performance' for the multivariate Marker is the averaged performance of many such permutations; typically ten cross-validation rounds are used.

It is important to note that the purpose of Cross-Validation is to assess the generalizability of a Marker, within the limitations posed by the availability of a relatively limited number of independent samples. In the absence of independent samples from a different population of patients, the Cross-Validation Performance is an estimation of the performance of the Marker on an independent test set of samples. Such an extrapolation is made possible by measuring the performance of the Marker on the many permutations and combinations of subsets of the available samples; this process effectively simulates a situation in which many more samples are available.

Figure 6:
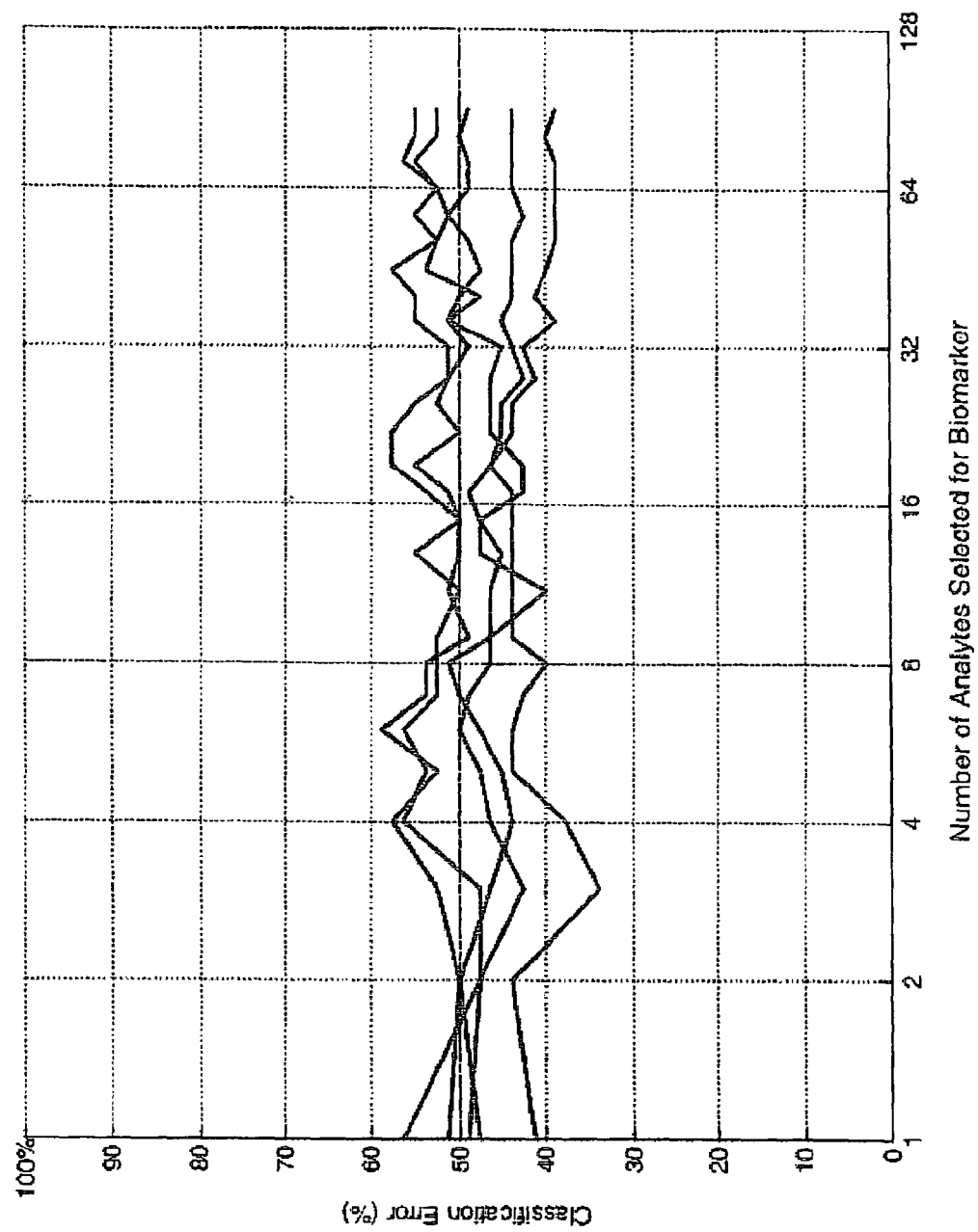
FIG. 6 shows an exemplary plot of "Permutation Analysis" on data sets as a function of the number of markers.

A second test of performance which has been applied for the processes outlined in this section is "Permutation Testing" which yields the "Permutation Performance". The "Permutation Performance" is the performance of the multivariate Marker selection algorithm when sample labels have been randomly permuted. This occurs over many such random permutations, and the average performance is reported. A robust classifier, namely one which is not overfit to the training set, should yield a Permutation Performance of approximately 50%; i.e. chance performance. The results of Permutation Testing are shown in FIG. 6, and indeed it is observed that the classification error is approximately 50% as expected. In FIG. 6, five (5) random class label permutations are shown. The algorithm described works from right to left—i.e. starting with 94 analytes and reducing by Recursive Feature Elimination until only one analyte remains. As expected from a model which is not overfit to the training data, each of the five permutation traces has classification errors around 50%, i.e. chance performance.

One multivariate marker selected in the manner described above comprised fifteen (15) analytes; these analytes together with their weighting coefficients are listed in Table 2 below.

TABLE 2

| Analyte | Coefficient (arb. units) |
|---|---|
| C18:3 Cholesterol ester | 0.42 |
| C32:1 Phosphatidylcholine | 0.33 |
| Alanine | 0.31 |
| Lipid (mainly VLDL) | 0.30 |
| Lysine | 0.30 |
| Hexadecanoic acid | 0.25 |
| C36:2 Phosphatidylcholine | 0.24 |
| Formate | 0.23 |
| C32:2 Phosphatidylcholine | 0.21 |
| C18:2 (Linoleic Acid) | 0.20 |
| Cholesterol | 0.18 |
| C18:2 Lyso-phosphatidylcholine | 0.18 |
| C36:3 Phosphatidylcholine | 0.17 |
| C34:4 Phosphatidylcholine | 0.04 |
| C34:3 Phosphatidylcholine | 0.01 |

For clarification, the analyte identified as "Lipid (mainly VLDL)" represents lipid derived primarily from Very Low Density Lipoprotein in the plasma, as measured using the NMR bioanalytical platform; this lipid is observed as a spectral peak appearing at a chemical shift of 1.55 ppm on the NMR spectrum, and this NMR peak arises due to a NMR resonance with the $CH_2CH_2CO$ structure of the lipid ("C" represents a carbon atom, "H2" represents two hydrogen atoms, "O" represents an oxygen atom).

Figure 7:
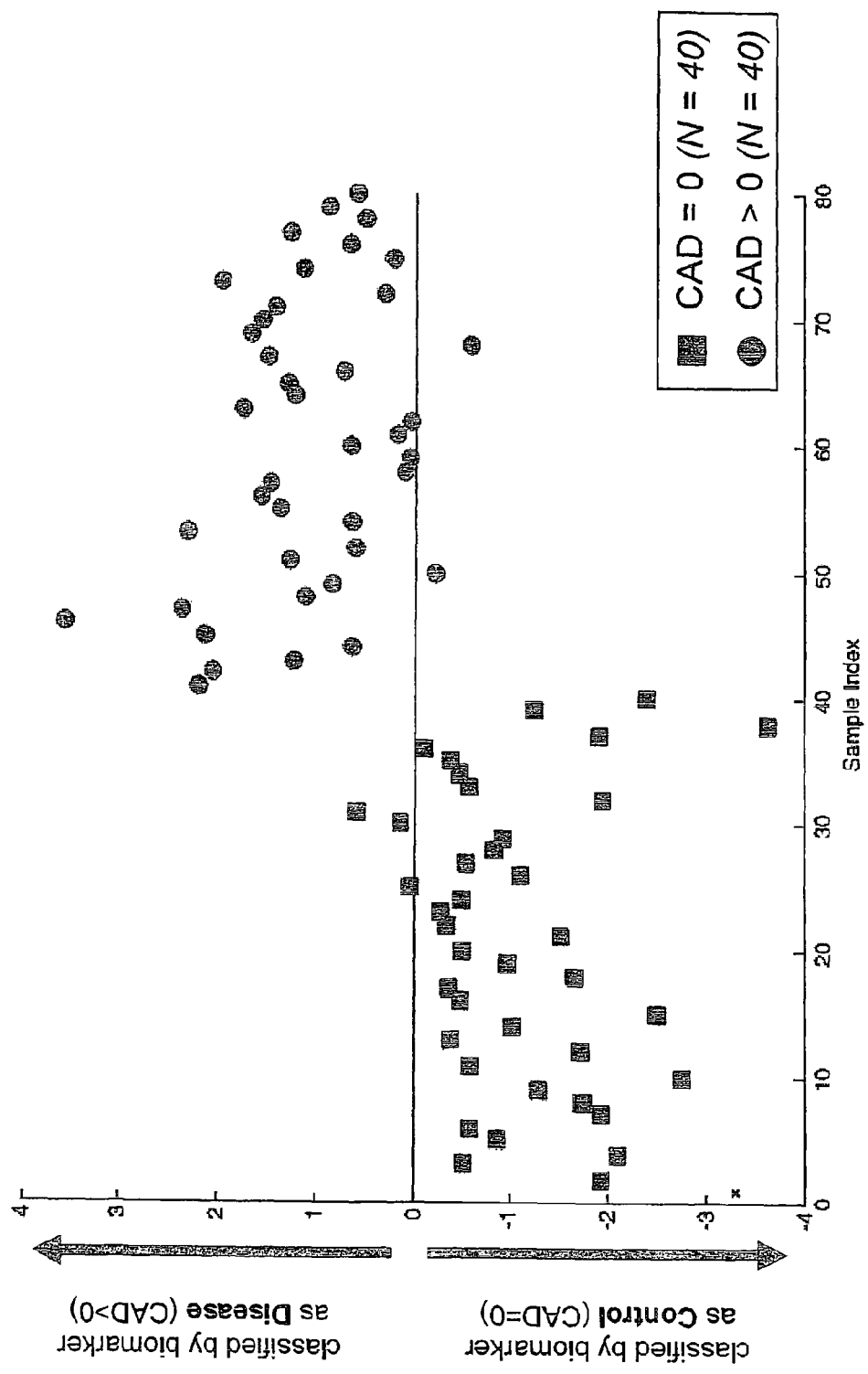
FIG. 7 shows an exemplary plot of subject classification based on the data presented in FIG. 4.

FIG. 7 shows the cross-validated performance of the multivariate marker comprising the analytes of Table 2 in classifying CAD=0 subjects from CAD>0 subjects. The square icons represent the CAD=0 samples, while the circle icons represent CAD>0 samples. The horizontal line represents the decision boundary; samples above the line are classified as 'CAD>0', while samples below the line are classified as 'CAD=0'. The cross-validated sensitivity and specificity are each greater than 90%.

Figure 8:
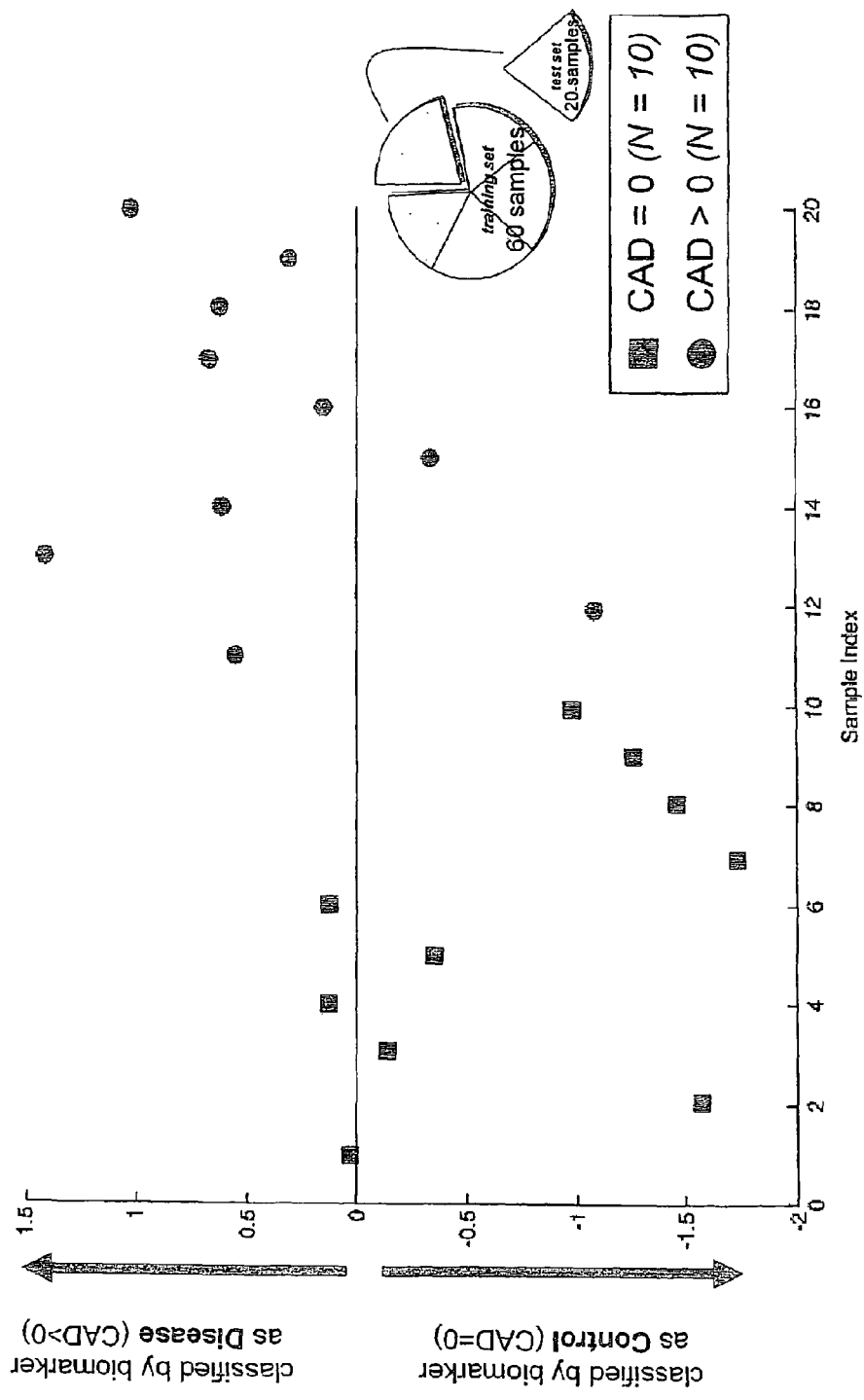
FIG. 8 shows an exemplary plot of subject classification based on one round of cross validation based on the data presented in FIG. 4.

A typical result from one round of "Cross Validation Performance" as described above is depicted graphically in FIG. 8. FIG. 8 represents an analysis using the multivariate marker comprising the analytes of Table 2 in classifying CAD=0 subjects from CAD>0 subjects. The square icons represent the CAD=0 samples, while the circle icons represent CAD>0 samples. The horizontal line represents the decision boundary; samples above the line are classified as 'CAD>0', while samples below the line are classified as 'CAD=0'. In this round of cross validation, twenty samples were left out of the analysis completely (ten CAD=0 samples and ten CAD>0 samples), and were subsequently classified using the analytes and coefficients listed in Table 2. The result is shown in FIG. 8. It is seen in FIG. 8 that there are three (3) false positives and two (2) false negatives, from this round of cross validation. The final sensitivity and specificity figures of merit for the multivariate marker are determined by many such iterations of cross validation, as described above.

Table 3 below is a summary of the results for classifying CAD>0 and CAD=0 subjects utilizing the fifteen (15) analyte multivariate marker of Table 2. "Cross-Validation" performance is as defined above. Values in parentheses are standard errors ("SE") calculated based on the underlying binomial distribution of total numbers of CAD>0 and CAD=0 samples correctly classified, and in units of percent. The standard errors of these estimates were approximated using the formula for the standard error of the corrected resampled t distribution [see V. N. Vapnik, Statistical Learning Theory, John Wiley & Sons, New York (1998)].

TABLE 3

Summary of performance of fifteen analyte multivariate marker in classifying CAD = 0 samples and CAD > 0 samples.

| Cross-Validation Sensitivity and SE (%) | Cross-Validation Specificity and SE (%) |
|---|---|
| 87.43% (8.93) | 89.10% (7.45) |

Multivariate Statistical Analysis: Principal Components Analysis

Figure 9:
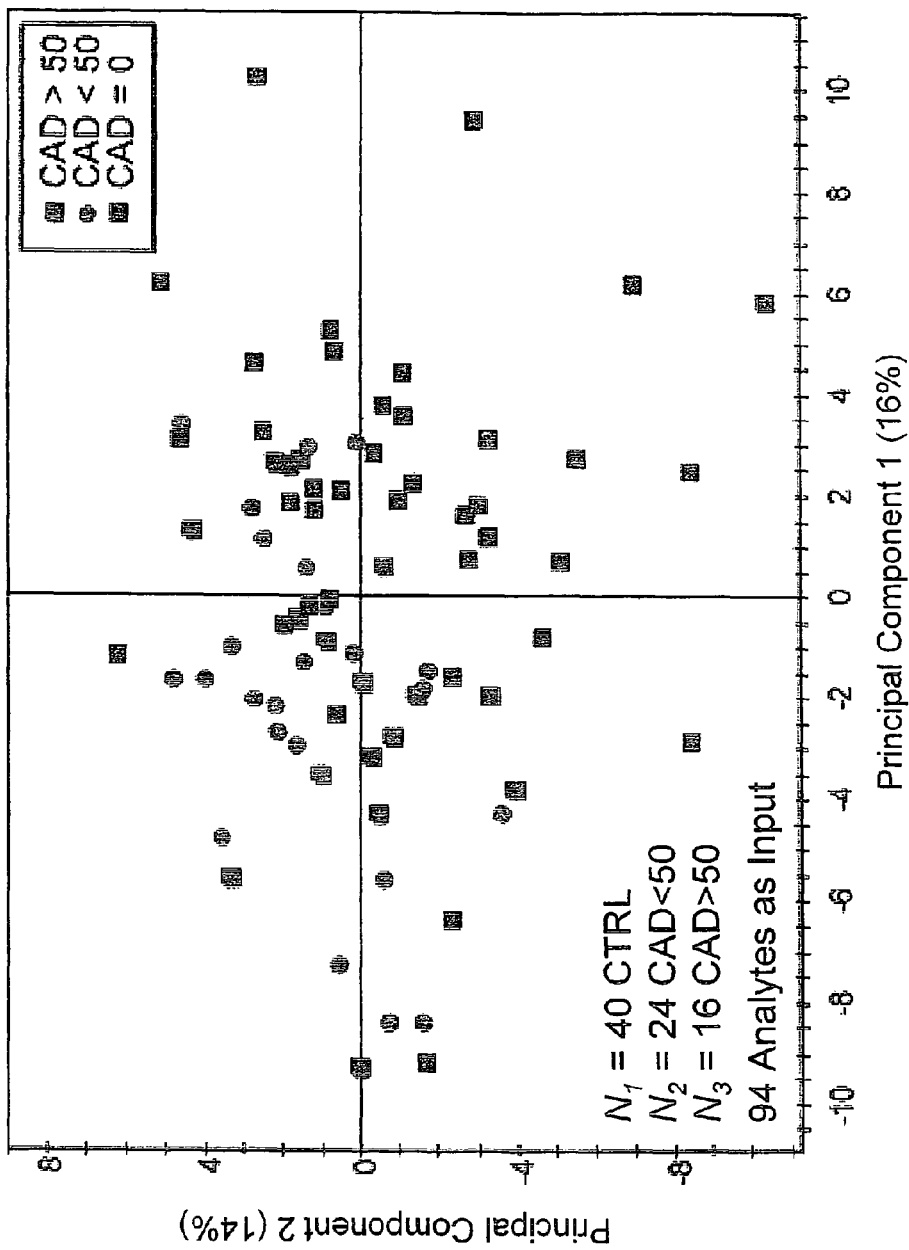
FIG. 9 shows an exemplary plot of principal components analysis.

Another multivariate data analysis methodology which was applied to the data set consisting of the ninety-four (94) identified analytes of Table 2, after the data alignment, normalization and pre-processing steps described above was "Principal Components Ananysis", hereafter referred to as "PCA". In contrast with classification approaches presented above, Principal Components Analysis is an unsupervised data analysis method [see Basilevsky A, "Statistical Factor Analysis and Related Methods, Theory and Applications" (1994) John Wiley & Sons, New York]. Based on the abundances of each of the ninety-four identified analytes listed in Table 2, a PCA analysis was performed, and a graphical representation comprising the first two principal components is shown in FIG. 9. In FIG. 9, each data point represents a sample from the study. It is seen that the CAD=0 samples are projected to predominantly the lower-right quadrant in the first two principal components. The first and second principal components explain 16% and 14% of the overall data set variance, respectively. For illustration, the CAD>0 samples are further categorized into two groups: (i) Coronary Artery Disease Prognostic Index greater than zero but less than 50, and (ii) Coronary Artery Disease Prognostic Index greater than or equal to 50 but less than 100.

Multivariate Statistical Analysis: Partial Least Squares Discriminant Analysis

Figure 10:
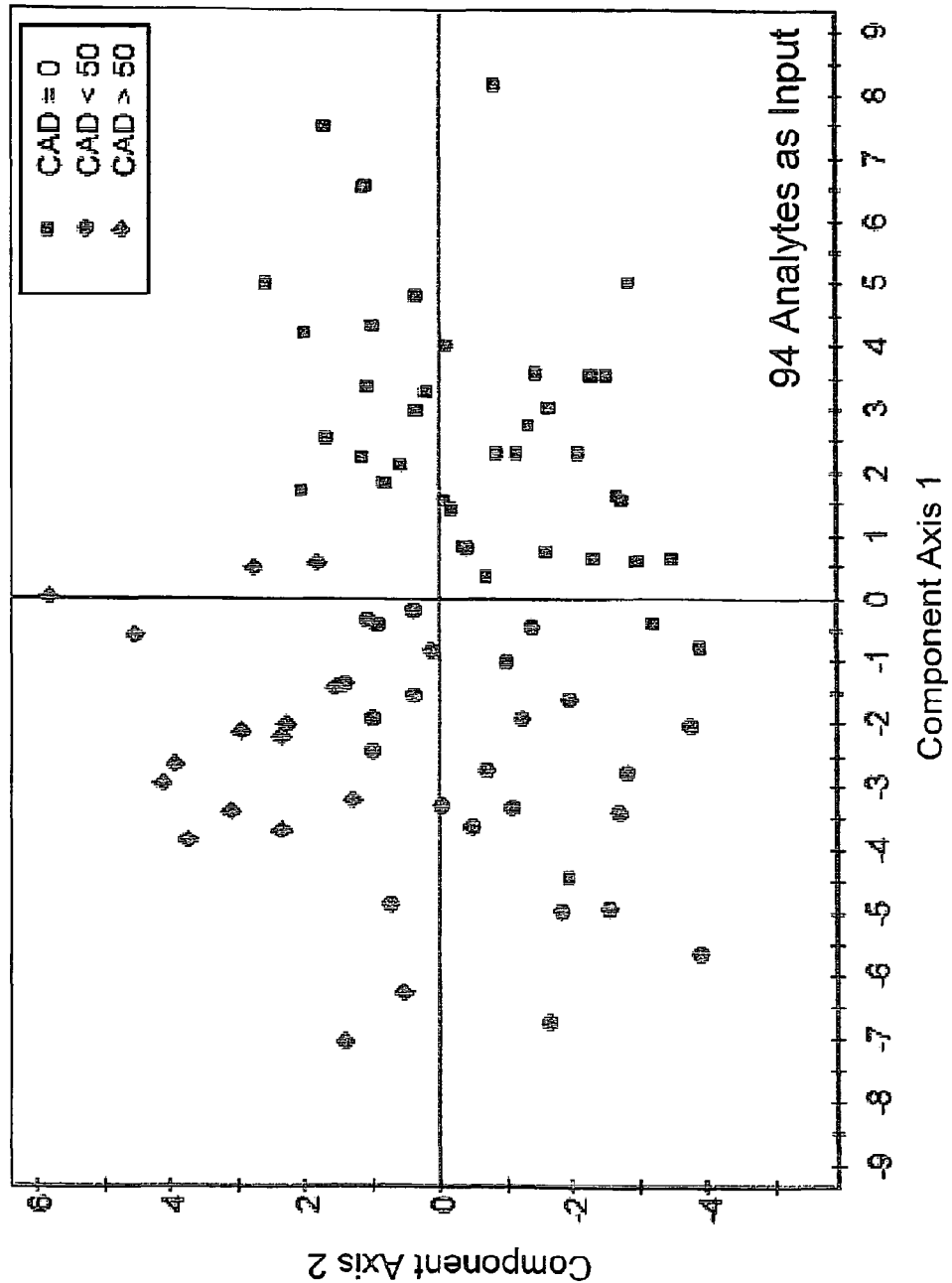
FIG. 10 shows an exemplary plot of partial least square discriminant analysis.

Another multivariate data analysis methodology which was applied to the data set consisting of the ninety-four (94) identified analytes of Table 2, after the data alignment, normalization and pre-processing steps described above was "Partial Least Squares Discriminant Analysis", hereafter referred to as "PLSDA". In contast with the PCA approach presented above, PLSDA is a supervised data analysis method; however in further contast to the Classification and Recursive Feature Elimination approach presented earlier, PLSDA does not involve Recursive Feature Elimination and utilizes the information content in all ninety-four analytes without eliminating any analytes from the analysis. For further information on PLSDA, see Eriksson L, Johansson E, Kettaneh-Wold N, and Wold S. (2001) "Multi- and Megavariate Data Analysis Principles and Applications," Umetrics A B, Umea, Sweden. (ISBN: 91-973730-1-X)]. In the PLSDA analysis which was carried out, the samples were further categorized into three (3) categories: (i) CAD=0, (ii) Coronary Artery Disease Prognostic Index greater than zero but less than 50, and (iii) Coronary Artery Disease Prognostic Index greater than or equal to 50 but less than 100. FIG. 10 graphically shows the first two discriminant axes from this PLSDA analysis. Each data point represents a sample from the study. It is seen that the three categories of samples enumerated above are projected to different subspaces in the figure. In addition, the separation between the severely diseased patients (Coronary Artery Disease Prognostic Index greater than or equal to 50) and the CAD=0 patients is greater than the separation between the Coronary Artery Disease Prognostic Index greater than zero but less than 50 group and the CAD=0 group, reproducing the ordinal nature of the Coronary Artery Disease Prognostic Index.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

INCORPORATION BY REFERENCE

The entire disclosure of each of the aforementioned patent and scientific documents cited hereinabove is expressly incorporated by reference herein.

What is claimed is:

1. A method of screening a human individual for having or being at risk for developing coronary artery disease, the method comprising:
measuring the amount of at least fifteen analytes in a sample comprising plasma from the individual, wherein the at least fifteen analytes comprise: C18:3 cholesterol ester, C32:1 phosphatidylcholine, alanine, very low density lipoprotein, lysine, hexadecanoic acid, C36:2 phosphatidylcholine, formate, C32:2 phosphatidylcholine, C18:2 linoleic acid, cholesterol, C18:2 lyso-phosphatidylcholine, C36:3 phosphatidylcholine, C34:4 phosphatidylcholine, and C34:3 phosphatidylcholine;
calculating a marker for the individual by weighting the measured analyte amounts, wherein calculating a marker comprises multiplying the amount of each of the at least fifteen analytes by an analyte coefficient to obtain an analyte value; and combining the analyte value of each measured analyte to obtain the marker; and
classifying the individual's risk of having or developing coronary artery disease based on the marker.

2. The method of claim 1, comprising normalizing the measured amount of each analyte to obtain a normalized amount.

3. The method of claim 1, wherein the step of classifying comprises comparing the marker to a standard.

4. The method of claim 1, wherein the step of classifying comprises comparing the marker to a decision boundary.

* * * * *